US 11,795,440 B2

(12) United States Patent
Tuller et al.

(10) Patent No.: US 11,795,440 B2
(45) Date of Patent: *Oct. 24, 2023

(54) ATTENUATED VIRUS MUTATED AT SITES OF EVOLUTIONARILY CONSERVED RNA STRUCTURE

(71) Applicants: RAMOT AT TEL-AVIV UNIVERSITY LTD., Tel Aviv (IL); YEDA RESEARCH AND DEVELOPMENT CO. LTD., Rehovot (IL); SYNVACCINE LTD., Tel Aviv (IL)

(72) Inventors: Tamir Tuller, Herzeliya Pituach (IL); Eli Goz, Herzlia (IL); Shimshi Atar, Kiryat-Ono (IL); Hadas Zur, Tel-Aviv (IL)

(73) Assignees: RAMOT AT TEL-AVIV UNIVERSITY LTD., Tel Aviv (IL); YEDA RESEARCH AND DEVELOPMENT CO. LTD., Rehovot (IL); SYNVACCINE LTD., Tel Aviv (IL)

( * ) Notice: Subject to any disclaimer, the term of this patent is extended or adjusted under 35 U.S.C. 154(b) by 118 days.

This patent is subject to a terminal disclaimer.

(21) Appl. No.: 17/467,265

(22) Filed: Sep. 5, 2021

(65) Prior Publication Data

US 2022/0010287 A1 Jan. 13, 2022

Related U.S. Application Data

(63) Continuation of application No. 15/764,691, filed as application No. PCT/IL2016/051069 on Sep. 29, 2016, now Pat. No. 11,111,481.

(60) Provisional application No. 62/234,822, filed on Sep. 30, 2015.

(51) Int. Cl.
| | |
|---|---|
| *C12N 7/00* | (2006.01) |
| *C12N 7/04* | (2006.01) |
| *A61K 39/12* | (2006.01) |
| *A61K 35/76* | (2015.01) |
| *G16B 99/00* | (2019.01) |
| *G16B 15/10* | (2019.01) |
| *A61K 39/00* | (2006.01) |

(52) U.S. Cl.
CPC .............. *C12N 7/00* (2013.01); *A61K 39/12* (2013.01); *C12N 7/04* (2013.01); *G16B 15/10* (2019.02); *G16B 99/00* (2019.02); *A61K 35/76* (2013.01); *A61K 2039/5254* (2013.01); *C12N 2770/24121* (2013.01); *C12N 2770/24162* (2013.01); *Y02A 50/30* (2018.01)

(58) Field of Classification Search
None
See application file for complete search history.

(56) References Cited

FOREIGN PATENT DOCUMENTS

WO 2008121992 A2 10/2008

OTHER PUBLICATIONS

Coleman JR, Papamichail D, Skiena S, Futcher B, Wimmer E, Mueller S. Virus attenuation by genome-scale changes in codon pair bias. Science. Jun. 27, 2008;320(5884):1784-7. doi: 10.1126/science.1155761. PMID: 18583614; PMCID: PMC2754401.

Sievers F, Wilm A, Dineen D, Gibson TJ, Karplus K, Li W, Lopez R, McWilliam H, Remmert M, Soding J, Thompson JD, Higgins DG. Fast, scalable generation of high-quality protein multiple sequence alignments using Clustal Omega. Mol Syst Biol. Oct. 11, 2011;7:539. doi: 10.1038/msb.2011.75. PMID: 21988835; PMCID: PMC3261699.

Altschul SF, Erickson BW. Significance of nucleotide sequence alignments: a method for random sequence permutation that preserves dinucleotide and codon usage. Mol Biol Evol. Nov. 1985;2(6):526-38. doi: 10.1093/oxfordjournals.molbev.a040370. PMID: 3870875.

Zhang Y, Ponty Y, Blanchette M, Lécuyer E, Waldispühl J. SPARCS: a web server to analyze (un)structured regions in coding RNA sequences. Nucleic Acids Res. Jul. 2013;41(Web Server issue):W480-5. doi: 10.1093/nar/gkt461. Epub Jun. 8, 2013. PMID: 23748952; PMCID: PMC3692110.

Lorenz R, Bernhart SH, Honer Zu Siederdissen C, Tafer H, Flamm C, Stadler PF, Hofacker IL. ViennaRNA Package 2.0 Algorithms Mol Biol. Nov. 24, 2011;6:26. doi: 10.1186/1748-7188-6-26. PMID: 22115189; PMCID: PMC3319429.

Mathews DH. Revolutions in RNA secondary structure prediction. J Mol Biol. Jun. 9, 2006;359(3):526-32. doi: 10.1016/j.jmb.2006.01.067. Epub Feb. 6, 2006. PMID: 16500677.

Mathews DH, Sabina J, Zuker M, Turner DH. Expanded sequence dependence of thermodynamic parameters improves prediction of RNA secondary structure. J Mol Biol. May 21, 1999;288(5):911-40. doi: 10.1006/jmbi.1999.2700. PMID: 10329189.

Wuchty S, Fontana W, Hofacker IL, Schuster P. Complete suboptimal folding of RNA and the stability of secondary structures. Biopolymers. Feb. 1999;49(2):145-65. doi: 10.1002/(SICI)1097-0282(199902)49:2<145::AID-BIP4>3.0.CO;2-G. PMID: 10070264.

(Continued)

*Primary Examiner* — Nicole Kinsey White
(74) *Attorney, Agent, or Firm* — The Roy Gross Law Firm, LLC; Roy Gross

(57) ABSTRACT

Attenuated viruses and methods of designing them are disclosed. In one embodiment, there is disclosed an attenuated form of a virulent virus comprising an RNA encoding a viral protein or a nucleic acid sequence transcribable to said RNA, wherein the folding energy or structure of the RNA is changed at positions of evolutionarily conserved RNA structures with respect to that of said RNA encoding said viral protein in the virulent virus so as to bring about attenuation of the virus.

20 Claims, 10 Drawing Sheets
(9 of 10 Drawing Sheet(s) Filed in Color)
Specification includes a Sequence Listing.

(56) References Cited

OTHER PUBLICATIONS

Zanini F, Neher RA. Quantifying selection against synonymous mutations in HIV-1 env evolution. J Virol. Nov. 2013;87(21):11843-50. doi: 10.1128/JVI.01529-13. Epub Aug. 28, 2013. PMID: 23986591; PMCID: PMC3807363.

Jackson RJ. Alternative mechanisms of initiating translation of mammalian mRNAs. Biochem Soc Trans. Dec. 2005;33(Pt 6):1231-41. doi: 10.1042/BST20051231. PMID: 16246087.

Selby CP, Drapkin R, Reinberg D, Sancar A. RNA polymerase II stalled at a thymine dimer: footprint and effect on excision repair. Nucleic Acids Res. Feb. 15, 1997;25(4):787-93. doi: 10.1093/nar/25.4.787. PMID: 9016630; PMCID: PMC146523.

Tuller T, Zur H. Multiple roles of the coding sequence 5' end in gene expression regulation. Nucleic Acids Res. Jan. 2015;43(1):13-28. doi: 10.1093/nar/gku1313. Epub Dec. 12, 2014. PMID: 25505165; PMCID: PMC4288200.

Alcaraz-Estrada, S. L., Yocupicio-Monroy, M., & Del Angel, R. M. (2010). Insights into dengue virus genome replication. Future Virology, 5(5), 575-592.

Zuker M, Stiegler P. Optimal computer folding of large RNA sequences using thermodynamics and auxiliary information. Nucleic Acids Res. Jan. 10, 1981;9(1):133-48. doi: 10.1093/nar/9.1.133. PMID: 6163133; PMCID: PMC326673.

Nussinov R. Strong doublet preferences in nucleotide sequences and DNA geometry. J Mol Evol. 1984;20(2):111-9. doi: 10.1007/BF02257371. PMID: 6433029.

Workman C, Krogh A. No evidence that mRNAs have lower folding free energies than random sequences with the same dinucleotide distribution. Nucleic Acids Res. Dec. 15, 1999;27(24):4816-22. doi: 10.1093/nar/27.24.4816. PMID: 10572183; PMCID: PMC148783.

Rivas E, Eddy SR. Secondary structure alone is generally not statistically significant for the detection of noncoding RNAs. Bioinformatics. Jul. 2000;16(7):583-605. doi: 10.1093/bioinformatics/16.7.583. PMID: 11038329.

Clyde K, Harris E. RNA secondary structure in the coding region of dengue virus type 2 directs translation start codon selection and is required for viral replication. J Virol. Mar. 2006;80(5):2170-82. doi: 10.1128/JVI.80.5.2170-2182.2006. PMID: 16474125; PMCID: PMC1395379.

Goz E, Tuller T. Widespread signatures of local mRNA folding structure selection in four Dengue virus serotypes. BMC Genomics. 2015;16 Suppl 10(Suppl 10):S4. doi: 10.1186/1471-2164-16-S10-S4. Epub Oct. 2, 2015. PMID: 26449467; PMCID: PMC4602183.

Kobayashi Y, Dadonaite B, van Doremalen N, Suzuki Y, Barclay WS, Pybus OG. Computational and molecular analysis of conserved influenza A virus RNA secondary structures involved in infectious virion production. RNA Biol. Sep. 2016;13(9):883-94.doi: 10.1080/15476286.2016.1208331. Epub Jul. 11, 2016. PMID: 27399914; PMCID: PMC5013999.

Shen, S. H., Futcher, B., Yang, C., & Wimmer, E. (2014). Synthetic Biology Approaches for Vaccine Development. Encyclopedia of Molecular Cell Biology and Molecular Medicine, 1-27. doi:10.1002/3527600906.mcb.20120059.

Meyers, R. A. (Jun. 8, 2015). Synthetic Biology, 2 Volumes (Current Topics from the Encyclopedia of Molecular Cell Biology and Molecular Medicine) (1st ed.). Wiley-Blackwell.

ATTENUATED VIRUS MUTATED AT SITES OF EVOLUTIONARILY CONSERVED RNA STRUCTURE

RELATED APPLICATIONS

This application is a continuation of U.S. Ser. No. 15/764,691 filed Mar. 29, 2018, which is a National Phase of PCT Patent Application No. PCT/IL2016/051069 having International filing date of Sep. 29, 2016, which claims the benefit of priority from U.S. Patent Application No. 62/234,822 filed on Sep. 30, 2015 entitled ATTENUATED VIRUS MUTATED AT SITES OF EVOLUTIONARILY CONSERVED RNA STRUCTURE. The contents of the above applications are all incorporated by reference as if fully set forth herein in their entirety.

FIELD AND BACKGROUND OF THE INVENTION

The present invention, in some embodiments thereof, relates to an attenuated virus comprising modified viral genome containing a plurality of nucleotide substitutions.

Viruses have always been one of the main causes of death and disease in man. Unlike bacterial diseases, viral diseases are not susceptible to antibiotics and are thus difficult to treat. Accordingly, vaccination has been humankind's main and most robust defense against viruses. Today, some of the oldest and most serious viral diseases such as smallpox and poliomyelitis (polio) have been eradicated (or nearly so) by world-wide programs of immunization. However, many other old viruses such as rhinovirus and influenza virus are poorly controlled, and still create substantial problems, though these problems vary from year to year and country to country. In addition, relatively newer viruses, such as Human Immunodeficiency Virus (HIV) and Severe Acute Respiratory Syndrome (SARS) virus, regularly appear in human populations and often cause deadly pandemics. There is also a potential for lethal man-made or man-altered viruses for intentional introduction as a means of warfare or terrorism.

Effective manufacture of vaccines remains an unpredictable undertaking. There are three major kinds of vaccines: subunit vaccines, inactivated (killed) vaccines, and attenuated live vaccines. For a subunit vaccine, one or several proteins from the virus (e.g., a capsid protein made using recombinant DNA technology) are used as the vaccine. Subunit vaccines produced in *Escherichia coli* or yeast are very safe and pose no threat of viral disease. Their efficacy, however, can be low because not all of the immunogenic viral proteins are present, and those that are present may not exist in their native conformations.

Inactivated (killed) vaccines are made by growing more-or-less wild type (wt) virus and then inactivating it, for instance, with formaldehyde (as in the Salk polio vaccine). A great deal of experimentation is required to find an inactivation treatment that kills the entire virus and yet does not damage the immunogenicity of the particle. In addition, residual safety issues remain in that the facility for growing the virus may allow a virulent virus to escape or the inactivation may fail.

An attenuated live vaccine comprises a virus that has been subjected to mutations rendering it to a less virulent and usable for immunization. Live, attenuated viruses have many advantages as vaccines: they are often easy, fast, and cheap to manufacture; they are often easy to administer (the Sabin polio vaccine, for instance, was administered orally on sugar cubes); and sometimes the residual growth of the attenuated virus allows "herd" immunization (immunization of people in close contact with the primary patient). These advantages are particularly important in an emergency, when a vaccine is rapidly needed. The major drawback of an attenuated vaccine is that it has some significant frequency/probability of reversion to wt virulence. For example, for this reason, the Sabin vaccine is no longer used in the United States.

To overcome the numerous pitfalls attributed to the classical vaccine design strategies, more efficient and robust rational approaches based on computer-based methods are highly desirable. One direction in designing in-silico vaccine candidates may be based on exploiting the synonymous information encoded in the genomes for attenuating the viral replication cycle while retaining the wild type proteins.

Some existing computational strategies may propose methods for designing life attenuated viral strains by using the additional layer of information carried by the distribution of codons encoding the viral proteome [1].

However, these have been tested only on a limited variety of viruses, were based on specific global features encoded in the genomes (while ignoring other important, possibly local, factors), and did not take into consideration the evolutionary dynamics as a general determinant of a possible significance of various genomic features for the viral replication cycle.

Accordingly, there remains a need for a systematic approach to generating attenuated live viruses that have practically no possibility of reversion and thus provide a fast, efficient, and safe method of manufacturing a vaccine.

Relevant background art includes PCT Application No. WO 2008121992 and Synthetic Biology: Advances in Molecular Biology and Medicine, edited by Robert Allen Meyers, pages 590-618, 2015.

SUMMARY OF THE INVENTION

According to some embodiments of the invention, there is provided an attenuated form of a virulent virus comprising an RNA encoding a viral protein or a nucleic acid sequence transcribable to the RNA, wherein the folding energy or structure of the RNA is changed at positions of evolutionarily conserved RNA structure with respect to that of the RNA encoding the viral protein in the virulent virus so as to bring about attenuation of the virus.

According to some embodiments of the invention, there is provided a method of making an attenuated viral genome comprising modifying the codon usage of the protein encoding region of a genome of a virulent virus so as to encode an RNA having a sufficient change in folding energy at sites of evolutionarily conserved RNA structure so as to bring about attenuation of the viral genome.

According to some embodiments of the invention, there is provided a computing platform for determining sites of modification to generate an attenuated virus comprising:
  (a) a data-storage device storing the nucleic acid sequence of the protein coding region of the genome of virulent viruses; and
  (b) a first processing unit for determining sites of evolutionarily conserved RNA structure; and
  (c) a second processing unit for determining a modification to the nucleic acid sequence which brings about a sufficient change in folding energy to attenuate the virus without changing the amino acid sequence of the coding region of the genome of the virulent virus.

According to some embodiments of the invention, there is provided a method of making an attenuated virus comprising inserting an attenuated viral generated according to the methods described herein into a host organism, thereby generating the attenuated virus.

According to some embodiments of the invention, there is provided a vaccine comprising the virus described herein and a pharmaceutically acceptable carrier.

According to some embodiments of the invention, there is provided a method for eliciting a protective immune response in a subject comprising administering to the subject a prophylactically or therapeutically effective dose of the vaccine described herein, thereby eliciting a protective immune response in the subject.

According to some embodiments of the invention, there is provided a method of immunizing a subject against a virus-associated disease comprising administering to the subject a prophylactically effective dose of the vaccine described herein, thereby immunizing the subject against the virus-associated disease.

According to some embodiments of the invention, the positions comprise at least 3 positions.

According to some embodiments of the invention, the viral protein is encoded by an amino acid sequence which is identical to the amino acid sequence encoded by the corresponding RNA of the virulent virus.

According to some embodiments of the invention, the virulent virus is a natural isolate.

According to some embodiments of the invention, the virulent virus is a mutant of a natural isolate.

According to some embodiments of the invention, the RNA is less than 90% identical to the corresponding RNA of the virulent virus.

According to some embodiments of the invention, the RNA is less than 80% identical to the corresponding RNA of the virulent virus.

According to some embodiments of the invention, the untranslated region of the RNA is identical to the untranslated region of the corresponding RNA of the virulent virus.

According to some embodiments of the invention, the virus infects an animal or a plant.

According to some embodiments of the invention, the animal is a human.

According to some embodiments of the invention, the virus induces a protective immune response in an animal host.

According to some embodiments of the invention, the RNA encodes more than one protein.

According to some embodiments of the invention, the viral protein is a capsid protein.

According to some embodiments of the invention, the virus is selected from the group consisting of dengue virus, poliovirus, rhinovirus, influenza virus, severe acute respiratory syndrome (SARS) coronavirus, Human Immunodeficiency Virus (HIV), Hepatitis C Virus (HCV), infectious bronchitis virus, Ebolavirus, Marburg virus, West Nile disease virus, Epstein-Barr virus (EBV) and yellow fever virus.

According to some embodiments of the invention, the virus is a flavivirus.

According to some embodiments of the invention, the flavivirus is a dengue virus.

According to some embodiments of the invention, the dengue virus is selected from the group consisting of dengue virus type 1, dengue virus type 2, dengue virus type 3 and dengue virus type 4.

According to some embodiments of the invention, the genome is encoded by a sequence selected from the group consisting of SEQ ID NOs: 1671-1734.

According to some embodiments of the invention, the virus is a retrovirus.

According to some embodiments of the invention, the retrovirus is human immunodeficiency virus (HIV).

According to some embodiments of the invention, the modifying the codon usage is effected by computationally selecting and exchanging codons encoding the same amino acid at sites of evolutionarily conserved RNA structure and computationally determining whether folding energy at the sites is changed by the exchanging.

According to some embodiments of the invention, the selecting and exchanging is repeated until the folding energy is changed by a predetermined level.

According to some embodiments of the invention, the selecting and exchanging is repeated until the folding energy is changed by a predetermined level at a predetermined number of positions.

According to some embodiments of the invention, the attenuated virus induces a substantially similar immune response in a host animal as the corresponding wild type virus.

According to some embodiments of the invention, the vaccine further comprises an adjuvant.

According to some embodiments of the invention, the subject has been exposed to a pathogenic virus.

According to some embodiments of the invention, the method further comprises administering to the subject at least one adjuvant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically (preferably computationally), or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
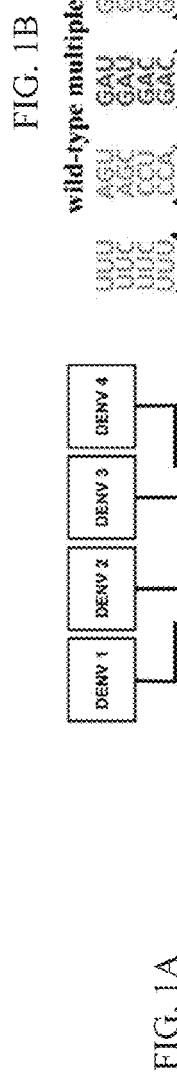
Figure 1B:
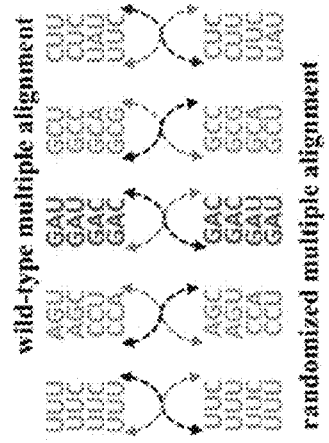
Figure 1C:
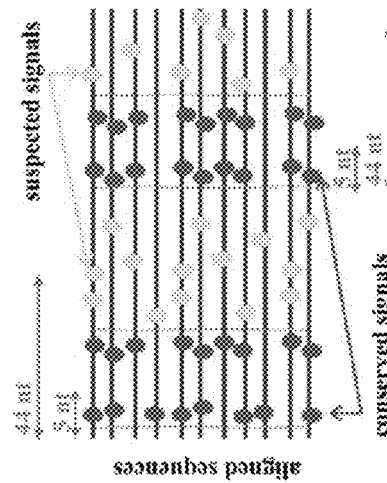
Figure 1E:
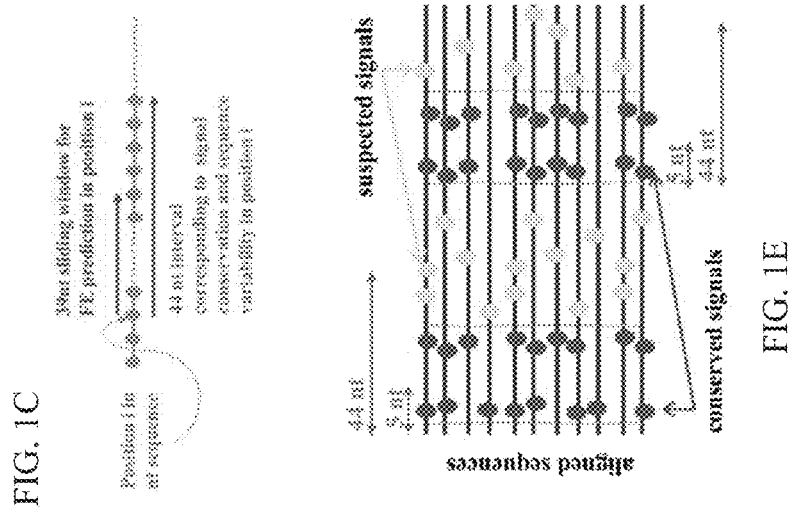
Figure 1D:
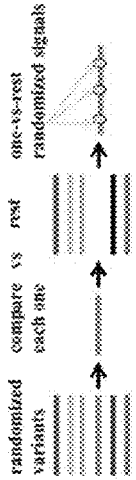

FIGS. 1A-E illustrate methods for identifying locations which overlap with evolutionary significant folding related signals which may be used for generating attenuated viruses according to embodiments of the present invention. FIG. 1A is a flow diagram illustrating how important secondary structures were identified on an example of Dengue virus. The method includes the following general steps (details are in the main text: I. Coding regions of 1,670 Dengue genomes from 4 different serotypes were collected. II. The coding regions were aligned. III. Each of the wild type sequences was randomized 1000 times based on two different randomization models (evolutionary, and dinucleotide constrained). IV. Local folding energy (FE) profiles were predicted for each wild type and randomized sequences separately. V. Profiles of sequence variability along the aligned coding regions were computed. VI. Wild type and randomized FE profiles were compared to identify positions suspected to have a strong/weak local folding signal (p-value<0.05). VII. Positions with FE signals significantly conserved across different viral variants were identified. FIG. 1B. Evolutionary-constrained randomization model—synonymous codons in each column in multiple alignment were permuted; if more than one amino acid was present (different colors) the permutations were restricted to the corresponding sets of synonymous codons. FIG. 1C. Prediction of FE in 39 nt windows (red arrow) along the coding sequence (brown); green arrow—44 nt sequence interval corresponding to signal conservation and sequence variability analyses (the size of the interval was determined by the FE prediction window size+allowed shift in signal position in conservation analysis). FIG. 1D. One-Versus-Rest (OVR) model—in each randomized variant, randomized FE signals were identified by a position-wise comparison to the rest of the randomized variants from the same wild-type origin. FIG. 1E. Signals conservation—suspected FE related signals (yellow) were defined as conserved if they appear in a significantly high (p-value<0.001 with respect to randomized conservation levels based on OVR randomized signals) number of different sequences within a 5 nt vicinity to each other (red). Two different clusters, each one consisting of two positions with a conserved FE related signal are illustrated (distinguished by vertical dot lines); by definition, positions belong to the same cluster if they correspond to 44 nt length partially-overlapping genomic windows.

Figure 2A:
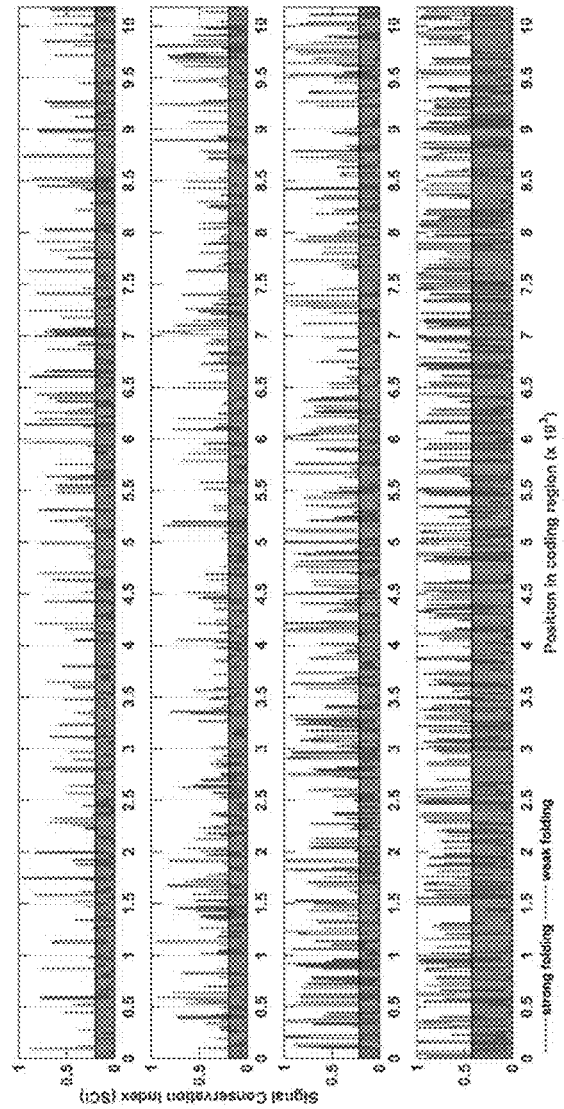
Figure 2B:
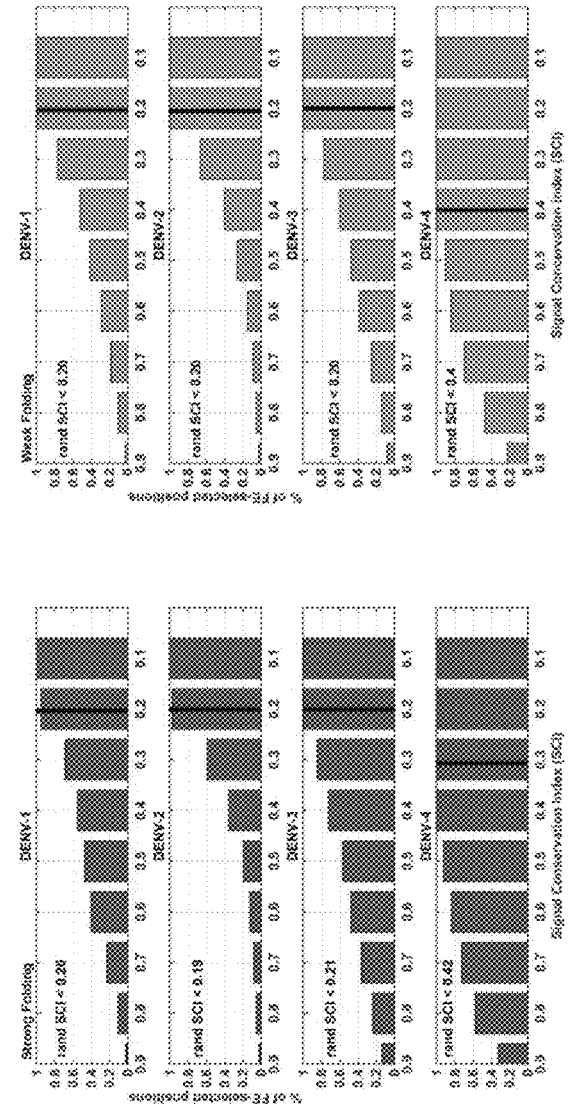

FIGS. 2A-B. A. Profiles of FE related signal conservation along the coding regions of 4 DENV serotypes for strong (red) and weak (green) folding. Positions with FSCI higher than a maximal value achieved in random (which is denoted by the shadowed area and is very similar for strong and weak folding) are not expected to be obtained by chance (p-value<0.001 with respect to FSCI values based on randomized signals; Benjamini-Hochberg fdr=0.001) and are defined as positions which may undergo a conserved selection for strong/weak local folding energy (shortly, minimum free folding energy (MFE)-selected). B. Distribution of FSCI values in MFE-selected positions for strong/weak folding in 4 serotypes. The maximal FSCI values achieved in random are explicitly annotated (rand SCI) and marked by black vertical bars. Total number of MFE-selected positions in wild-type is 40-100 folds higher than in random.

Figure 3:
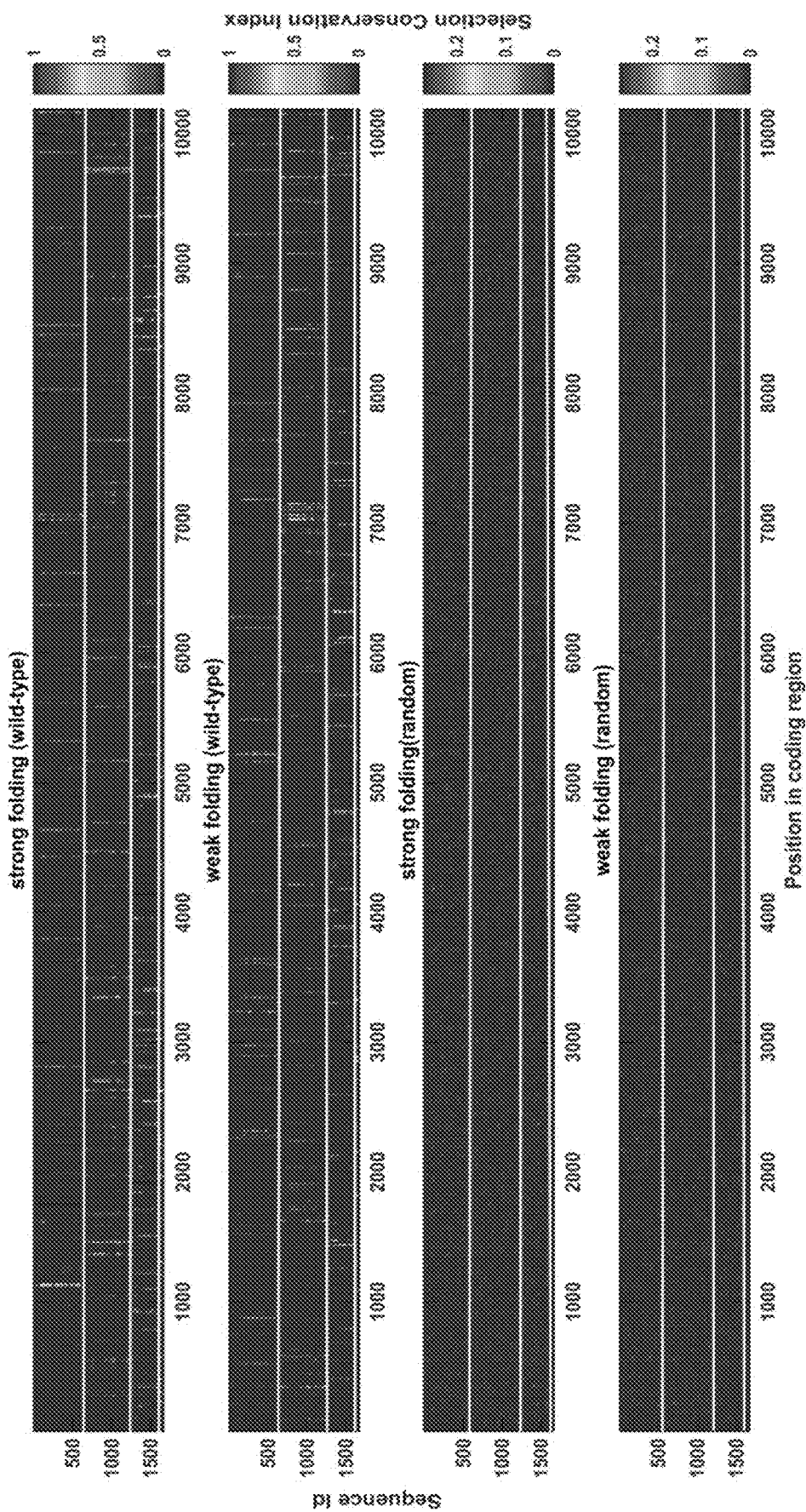

FIG. 3. Selection matrices for strong/weak folding for wild-type and one corresponding randomized variant in 4 DENV serotypes. Each row in the matrix corresponds to one sequence; columns are positions along the coding region. If sequence i has a suspected minimum free folding energy (MFE) related signal (p-value<0.05) in position j, the entry (i,j) has a value equal to the corresponding folding signal conservation index (FSCI); otherwise it is equal to zero. White horizontal lines separate between sequences belonging to different serotypes (serotypes are ordered from top to bottom, i.e. sequences 1-652 belong to serotype 1; 653-1268 to serotype 2; 1269-1625 to serotype 3 and 1626-1670 to serotype 4). We can clearly distinguish positions with conserved MFE related signals with different conservation levels in the wild-type, contrasting with a white noise resembling appearance in the randomized variants.

Figure 4A:
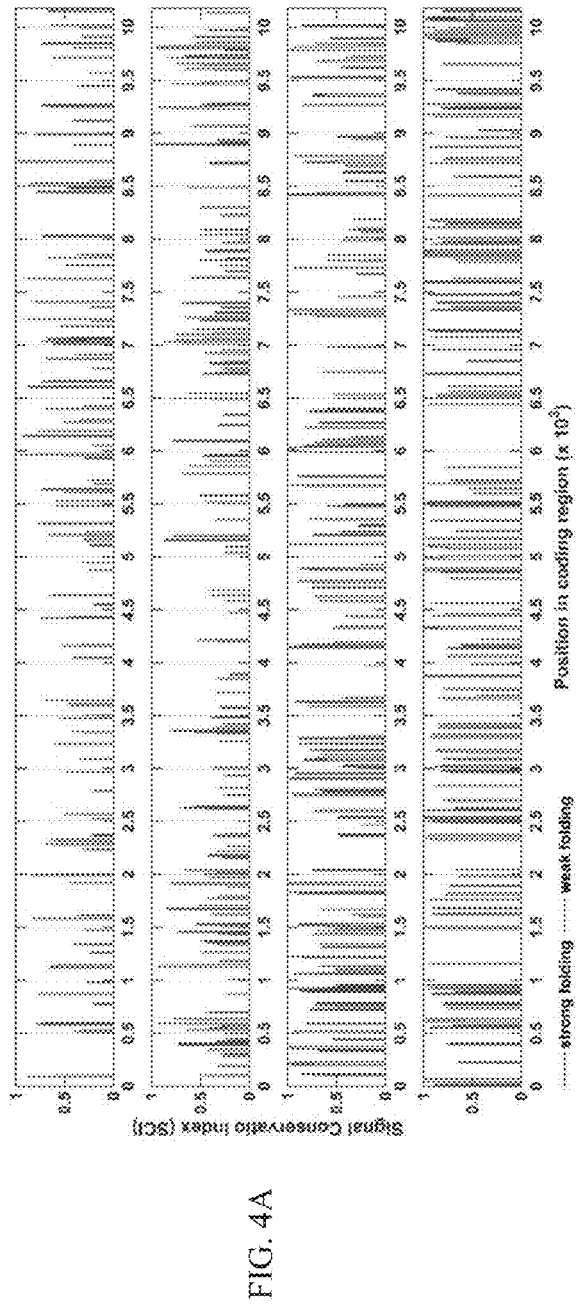
Figure 4B:
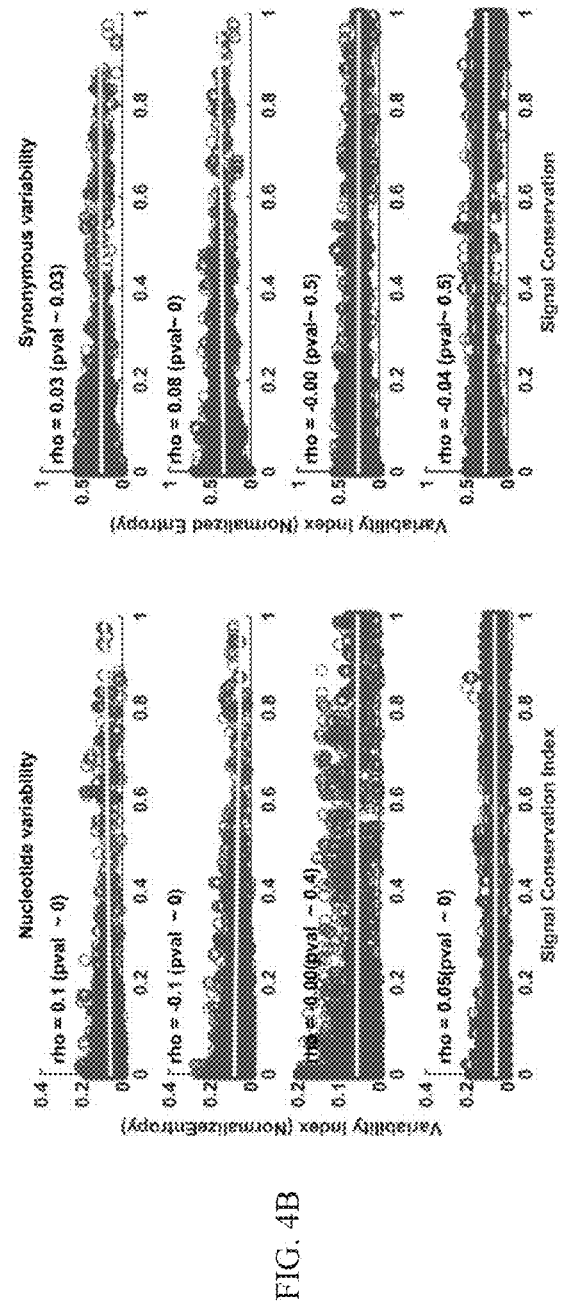

FIGS. 4A-B: A. Conserved selection for strong/weak folding related signals cannot be explained basing only on dinucleotide composition. As many as 60%, 52%, 49%, 34% of positions with conserved signals related to strong folding (red) and 62%, 58%, 43%, 44% of positions possessing weak folding signal conservation (green) (for serotypes 1-4 correspondingly) overlapped with MFE conserved signals identified with respect to dinucleotide-constrained randomization model, and this overlap was not likely to appear in random (p-value<0.001; no overlap was observed in 1000 randomized variants). B. The regions with significantly conserved strong/weak folding signal cannot be explained based only on sequence conservation. A low/insignificant Spearman correlation between conservation levels of MFE related signals and the nucleotide/synonymous variability in the corresponding genomic intervals.

Figure 5:
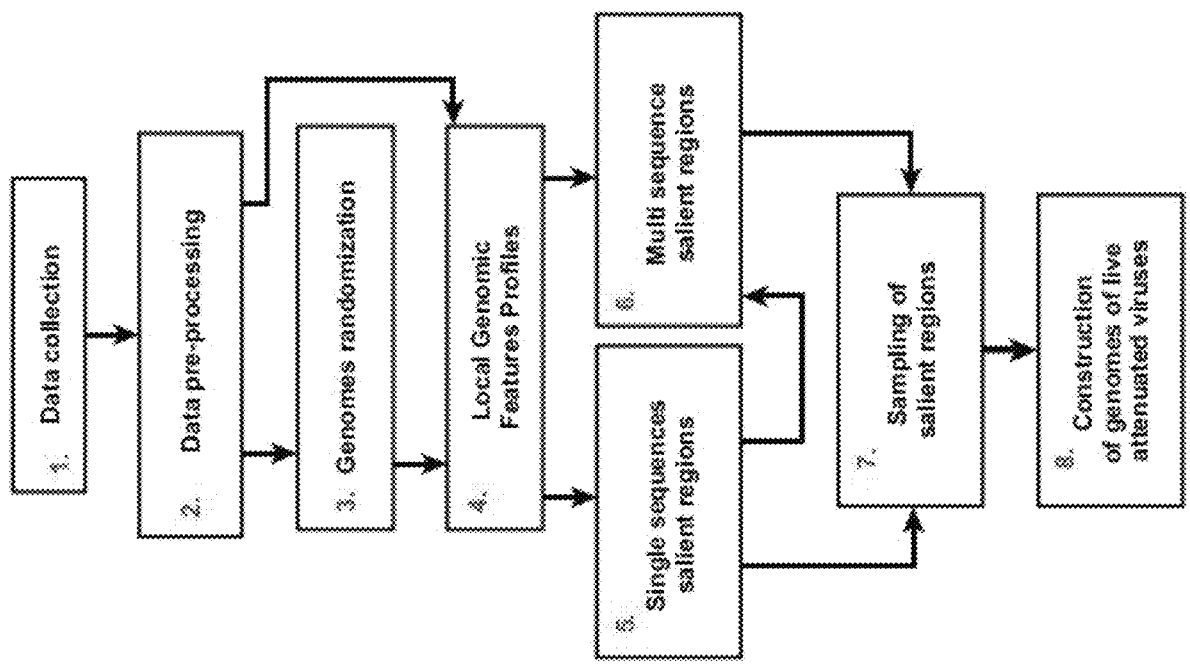

FIG. 5 is a flow diagram summarizing how attenuated viruses may be generated according to embodiments of the present invention. 1. Viral genomic sequences are collected from available resource. 2. The collected sequences are pre-processed: e.g., aligned and sub-sampled. 3. Each of the wild type sequences is randomized N times based on one or several biologically motivated randomization models. 4. Local genomic features (LGF) profiles are predicted for each wild type and random sequence separately. 5, 6. Wild type and randomized LGF profiles are compared to identify evolutionary salient local regions based on a single (5) or multiple (6) sequences. 7. K top salient regions are sampled according to their significance rank. 8. The resulting salient regions are mutated to construct the genome of live attenuated virus.

Figure 6A:
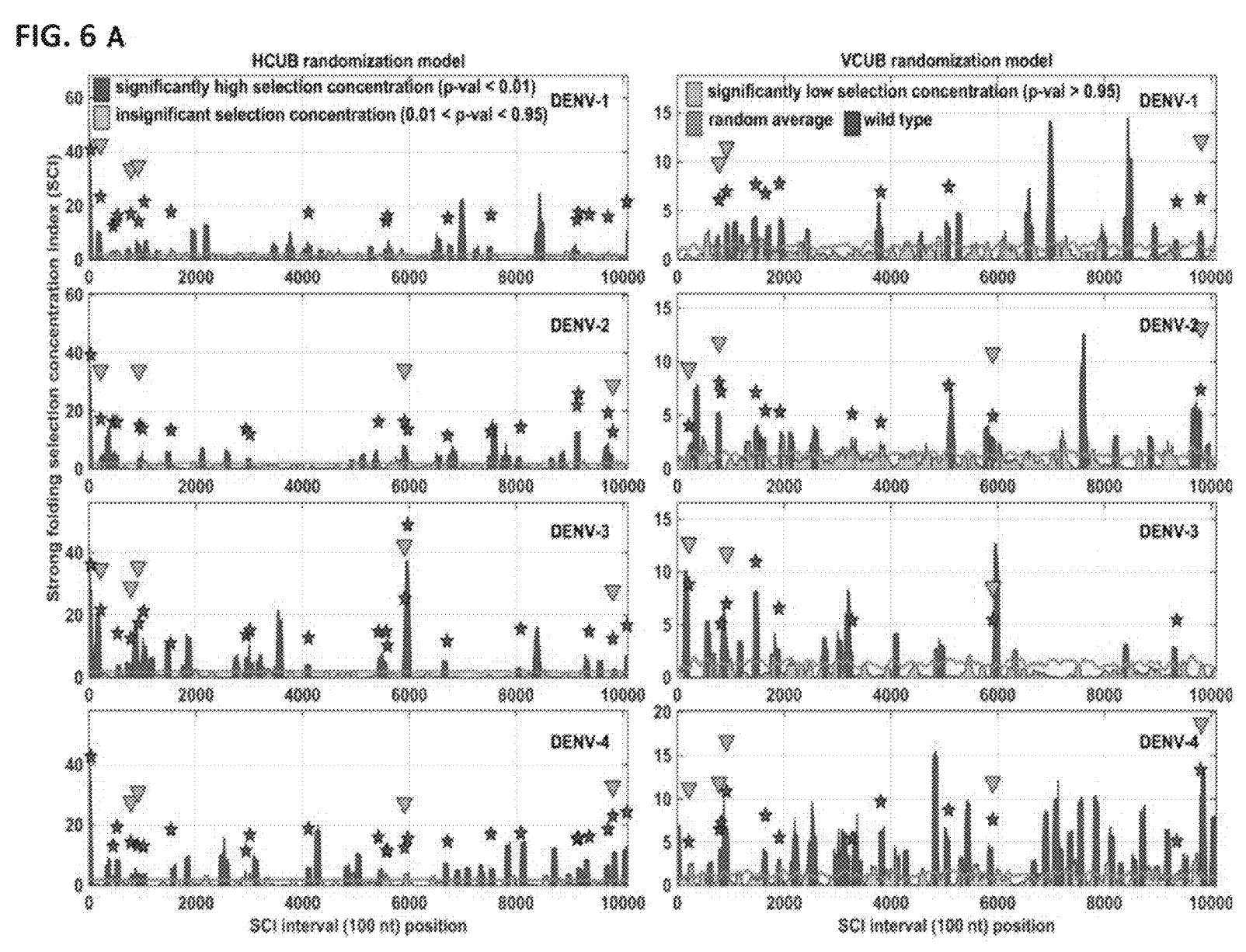
Figure 6:
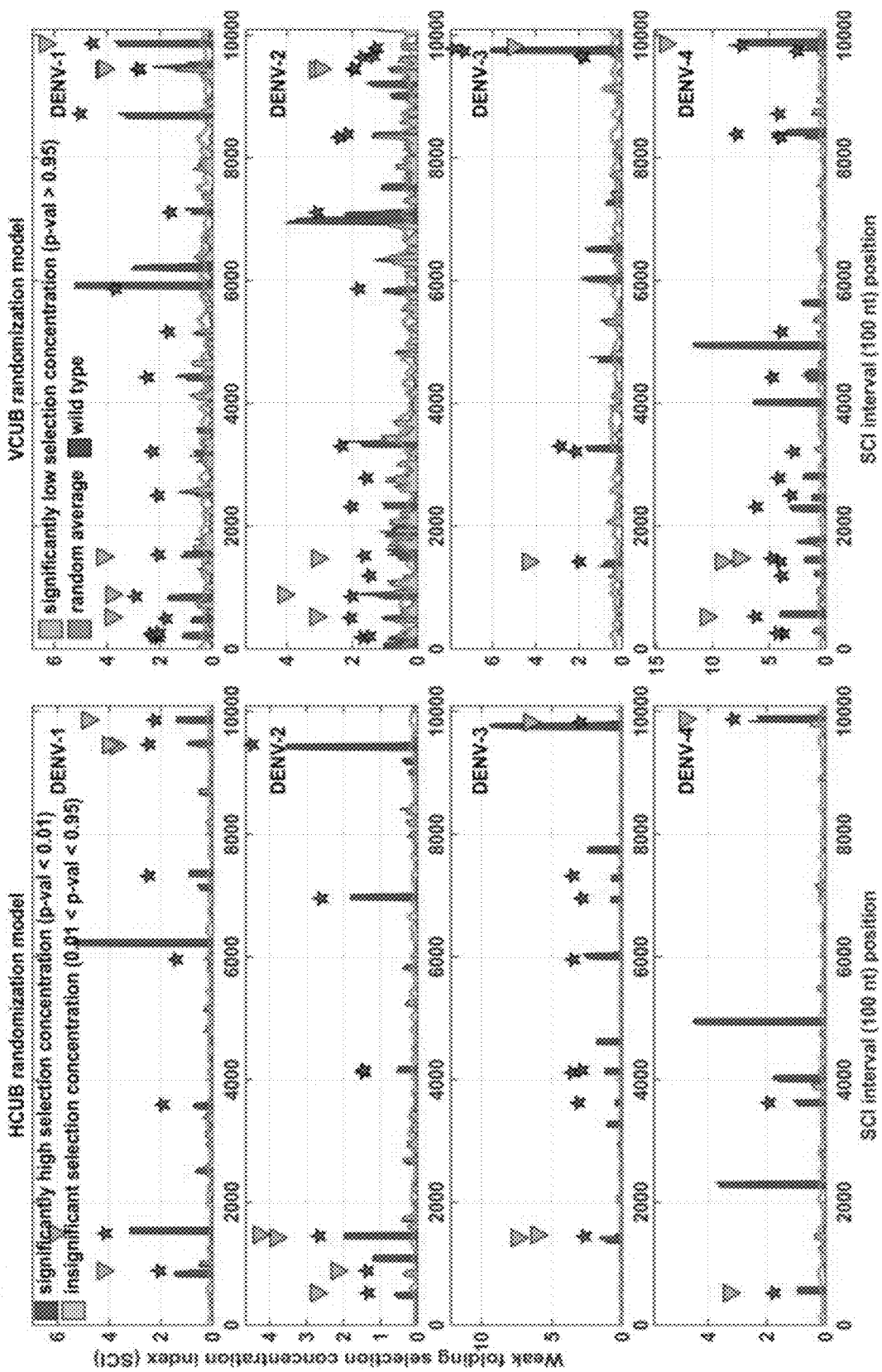

FIGS. 6A-B illustrate the selection concentration profiles of positions selected for strong/weak folding energy in coding regions of 4 Dengue virus serotypes. Selection concentration profiles (SCI-intervals of size 100) for serotypes 1-4 for strong (A) and weak (B) folding based on HCUB/VCUB randomization models: red—concentration intervals (p-values<0.01); blue—non-significant SCI-intervals (0.01<p-value<0.95); orange—SCI-intervals with significantly low SCI values (p-value>0.95); green—randomized selection concentration profile averaged over all randomized variants corresponding to all sequences in each serotype separately. Clusters of 100 nt concentration intervals (red), where the average number of positions selected for folding strength (weak or strong) is significantly higher than in random (p-value<0.01), are scattered all over the coding region. The number of salient regions in these clusters is on average ~3-20 times higher than in the corresponding randomized selection concentration profiles. The described concentrations of salient regions are not expected to appear in random, where salient regions are distributed almost uniformly over the coding region. Clusters which appear in at least 3 serotypes for strong folding and at least 2 serotypes for weak folding, with respect to the same random model (HCUB or VCUB) are marked with red pentagrams; clusters which appear in at least 3 serotypes for strong folding and at least 2 serotypes for weak folding, with respect to both random models (HCUB and VCUB), are marked by cyan triangles.

Figure 7:
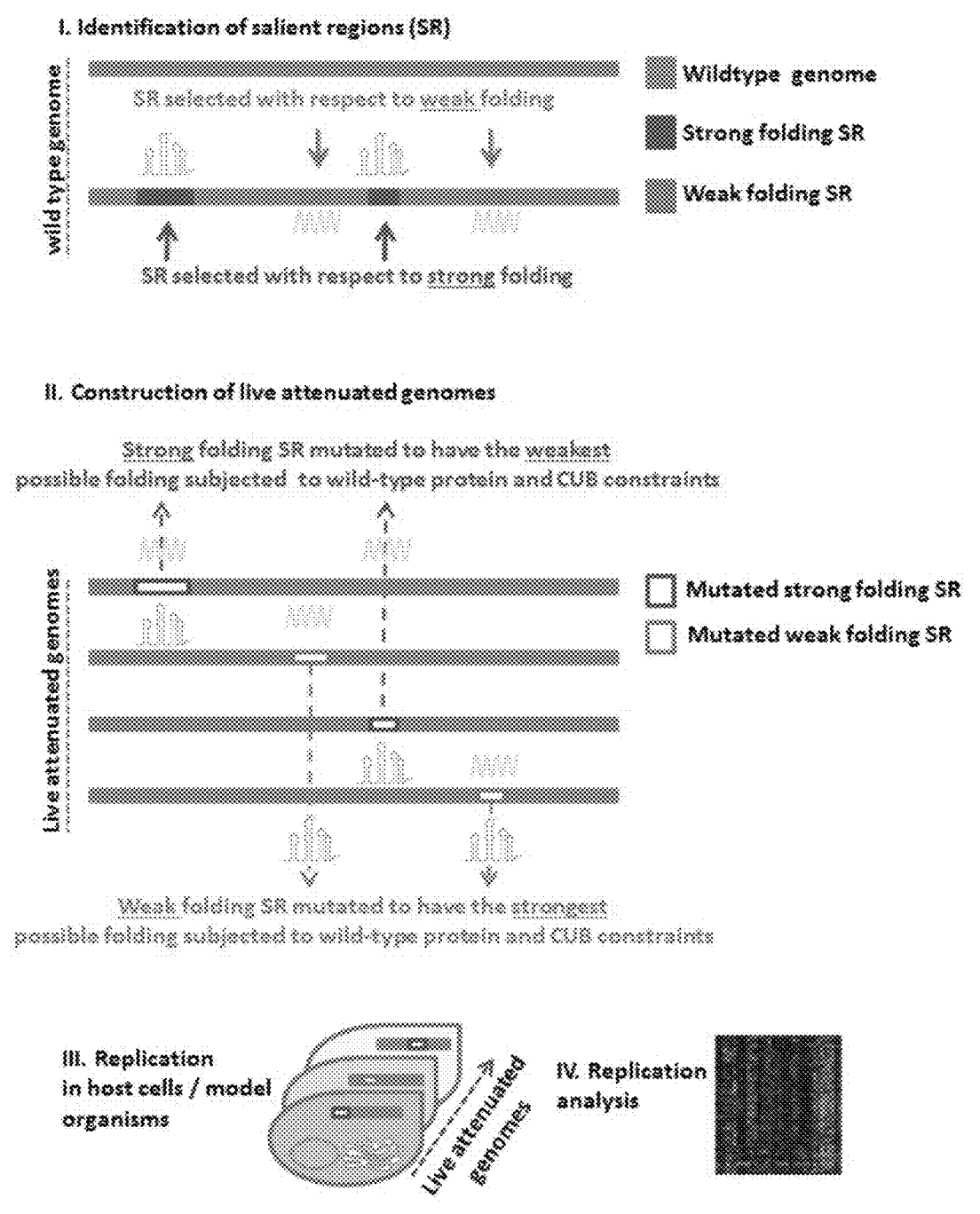

FIG. 7 illustrates the construction of genomes of live attenuated viruses by modifying the coding sequence in regions with a conserved selection for strong/weak folding: I. Salient regions in the wild type sequence, evolutionary selected to have a significantly strong/weak mRNA folding, are identified (See FIGS. 1A-E). II. Each one of the regions selected for strong folding is mutated in turn to have the weakest folding possible subjected to maintaining the encoded protein and the codon usage bias; each one of the regions selected for weak folding is mutated in turn to have the strongest folding possible subjected to maintaining the encoded protein and the codon usage bias; parts outside the mutated regions are not modified. The corresponding genomes of live attenuated viruses contain a mutated region (one mutated region per variant) and the rest of the sequence identical to the wild-type; other variants may contain compositions of several mutated regions and the rest of the sequence identical to the wild-type. III. Each live attenuated genome is replicated, at the beginning in corresponding cell lines and later in model organisms. III. Their replication rate is analyzed.

Figure 8A:
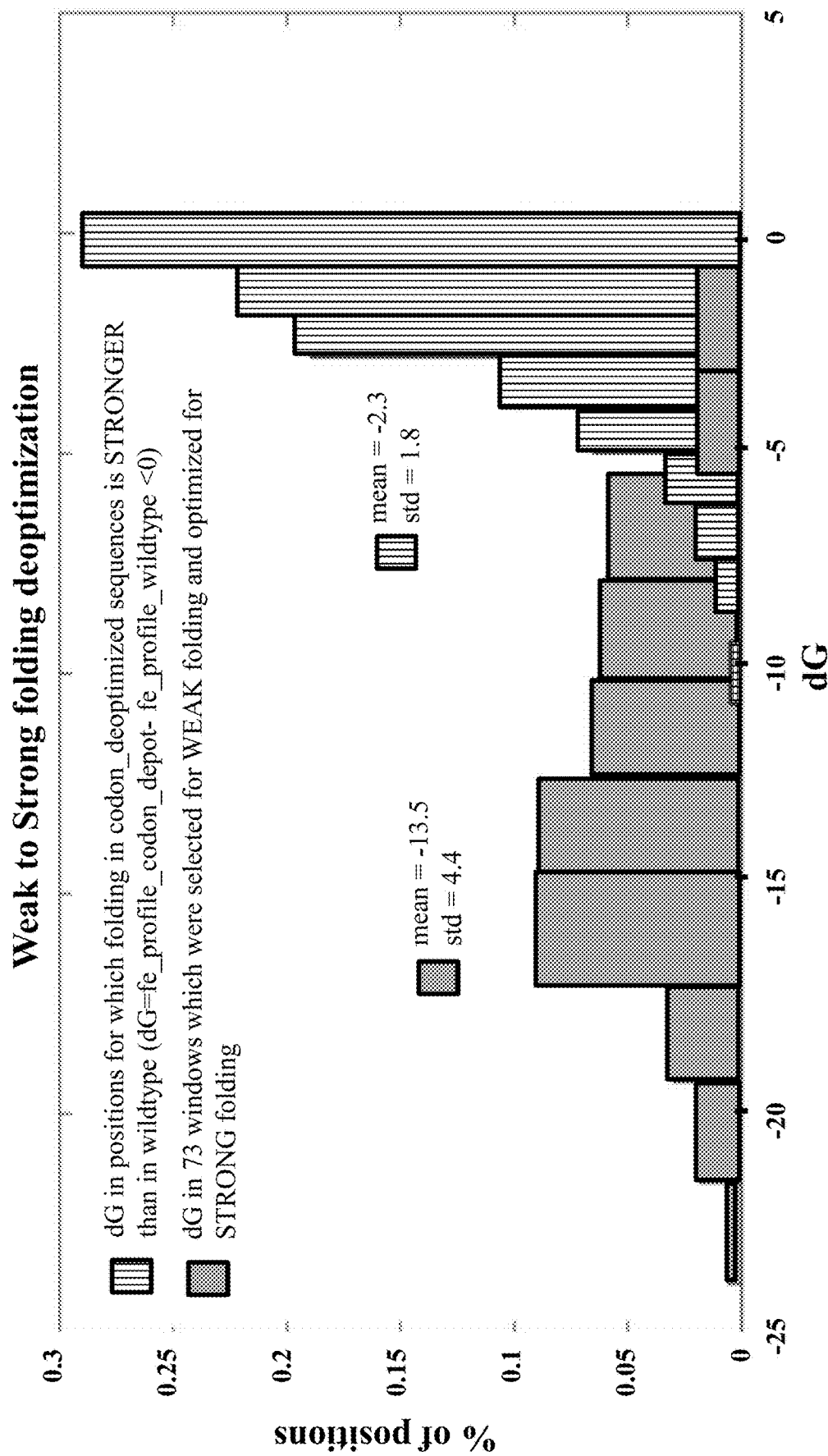
Figure 8B:
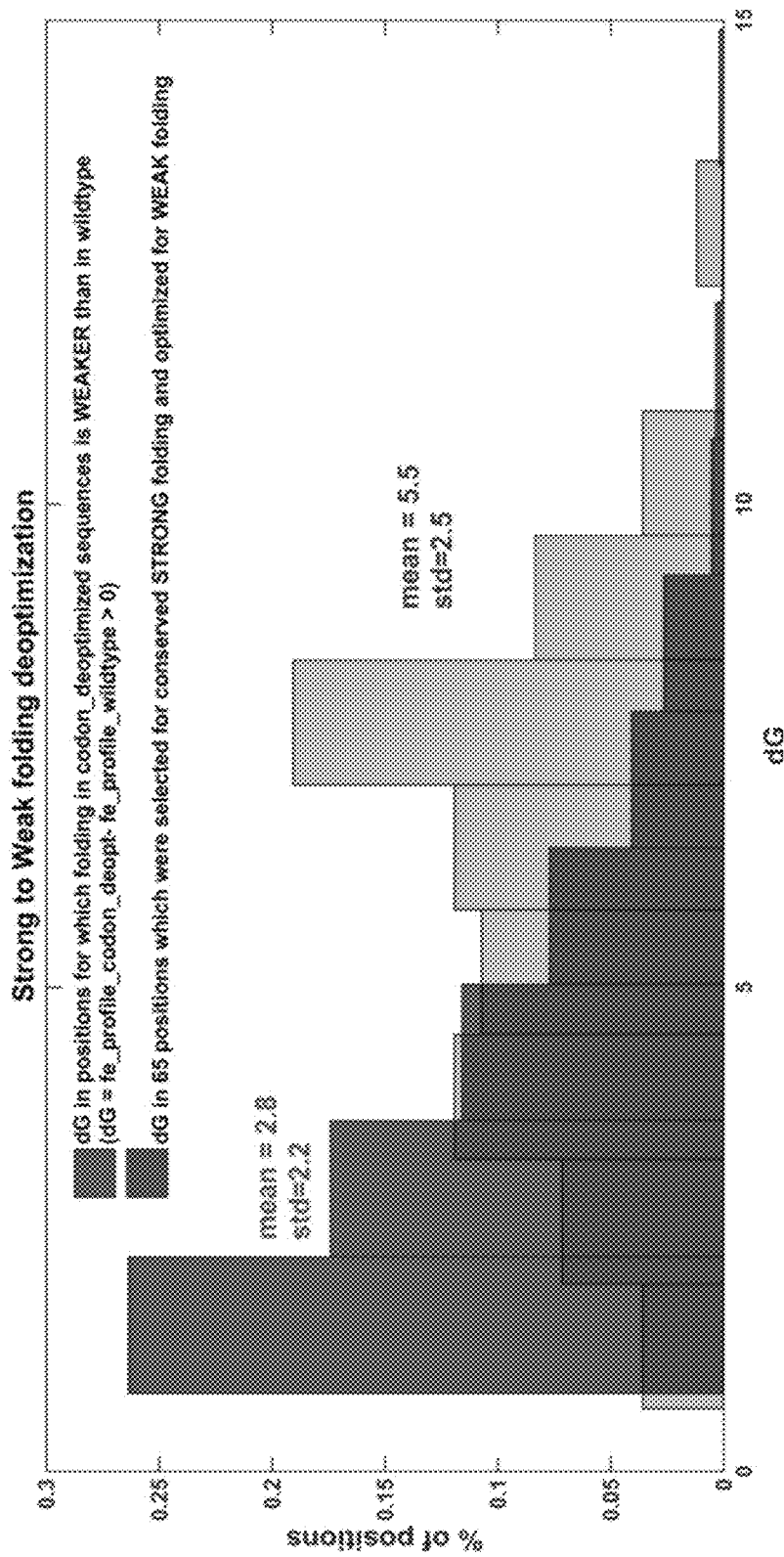

FIGS. 8A-B are graphs comparing the minimum free folding energy (ΔG) distributions for folding deoptimized and codon-pair deoptimized sequences. A. Strong to weak folding deoptimization: red—ΔG distribution in positions for which folding in codon pair deoptimized sequence is stronger than in wildtype; blue—ΔG distribution in 73 selected windows (with respect to weak folding) which have deoptimized to have strong folding. B. Weak to strong folding deoptimization. red—ΔG distribution in positions for which folding in codon pair deoptimized sequence is weaker than in wildtype; blue—ΔG distribution in 65 selected windows (with respect to strong folding) which have deoptimized to have weak folding.

DESCRIPTION OF SPECIFIC EMBODIMENTS OF THE INVENTION

The present invention, in some embodiments thereof, relates to an attenuated virus comprising a modified viral genome containing a plurality of nucleotide substitutions. The nucleotide substitutions result in the exchange of codons for other synonymous codons so as to bring about a change in the structure at multiple sites of evolutionarily conserved structures in the viral genome.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Viruses undergo a rapid evolutionary selection to evade the host immune systems, and to efficiently compete with endogenous transcripts of the host cell over the gene expression machinery. Mechanisms that facilitate efficient and selective viral replication are inherent in the nucleotide composition of the viral genomic sequence itself, and can involve the recruitment and/or modification of specific host factors.

Non-synonymous mutations which alter the amino acid sequence provide a distinct evolutionary advantage due to selective pressure, allowing viruses to escape from innate defense mechanisms and acquired immune surveillance of the host, and to rapidly adapt to new cell types, tissues, or species. Yet, genomes (and even coding sequences), both viral and of other organisms, not only code for protein products but also carry additional information encrypted in the composition of alternating codons. This information can be induced by synonymous mutations which preserve the underlying protein; being related to different biophysical and evolutionary characteristics, it may play an important regulatory role in different viral replication stages.

The present inventors aligned coding regions of different genomes from four DENV serotypes. Next, they designed randomized variants (a Null model) in silico, that preserved the amino acid order of the wild type sequences and further ensured that both the column-wise frequencies of synonymous codons at each position along their alignment and the distribution of frequencies of pairs of adjacent nucleotides (dinucleotides-constrained model) were maintained. They computed local folding energy profiles (FE-profiles) for each wild-type and randomized sequence. Using this approach, the present inventors identified hundreds of positions along the DENV coding regions that were selected during the course of viral evolution for significantly strong/weak folding (more/less negative FE). The present inventors reasoned that such positions may belong to functional elements (i.e. elements conserved in various genomes with respect to their function but not necessarily conserved with respect to their sequence) and therefore could have important implications for viral fitness.

The present inventors propose that altering the structure of viral RNA, by performing synonymous mutations at the identified locations would enable the altering of gene expression in a controllable way and eventually regulate the viral replication without affecting the encoded proteins. Accordingly the exemplified method can be used to design attenuated viruses that are too weak to cause illness but viable enough to replicate sufficiently and stimulate a robust immune response.

Thus, according to a first aspect of the present invention there is provided an attenuated form of a virulent virus comprising an RNA encoding a viral protein or a nucleic acid sequence transcribable to the RNA, wherein the folding energy or structure of the RNA is changed at positions of evolutionarily conserved structure with respect to that of the RNA encoding the viral protein in the virulent virus so as to bring about attenuation of the virus.

Any virus can be attenuated by the methods disclosed herein. The virus can be a dsDNA virus (e.g. Adenoviruses, Herpesviruses, Poxviruses), a single stranded "plus" (or positive) sense DNA virus (e.g., Parvoviruses) a double stranded RNA virus (e.g., Reoviruses), a single stranded+ (or positive) sense RNA virus (e.g. Dengue virus, Picornaviruses, Togaviruses), a single stranded "minus" (or negative) sense RNA virus (e.g. Orthomyxoviruses, Rhabdoviruses), a single stranded+ (or positive) sense RNA virus with a DNA intermediate (e.g. Retroviruses), or a double stranded reverse transcribing virus (e.g. Hepadnaviruses), or single stranded reverse transcribing virus (e.g. HIV).

According to a particular embodiment, the virus is a flavivirus.

Below is a non-limiting list of flaviviruses contemplated for attenuation according to embodiments of the present invention:

Tick-Borne Viruses:

Mammalian Tick-Borne Virus Group

Absettarov virus, Alkhurma virus (ALKV), Deer tick virus (DT), Gadgets Gully virus (GGYV), Kadam virus (KADV), Karshi virus, Kyasanur Forest disease virus (KFDV), Langat virus (LGTV), Louping ill virus (LIV), Omsk hemorrhagic fever virus (OHFV), Powassan virus (POWV), Royal Farm virus (RFV), Sokuluk virus (SOKV), Tick-borne encephalitis virus (TBEV), Turkish sheep encephalitis virus (TSE)

Seabird Tick-Borne Virus Group

Kama virus (KAMV), Meaban virus (MEAV), Saumarez Reef virus (SREV) and Tyuleniy virus (TYUV).

Mosquito-Borne Viruses:

Without known vertebrate host: *Aedes* flavivirus, Barkedji virus, Calbertado virus, Cell fusing agent virus, Chaoyang virus, *Culex* flavivirus, *Culex theileri* flavivirus, Donggang virus, Ilomantsi virus, Kamiti River virus, Lammi virus, Marisma mosquito virus, Nakiwogo virus, Nhumirim virus, Nounane virus, Spanish *Culex* flavivirus, Spanish Ochlerotatus flavivirus, Quang Binh virus Aroa Virus Group:

Aroa virus (AROAV), Bussuquara virus

Dengue virus group: Dengue virus (DENV), Kedougou virus (KEDV)

Japanese Encephalitis Virus Group:

Bussuquara virus, Cacipacore virus (CPCV), Koutango virus (KOUV), Ilheus virus (ILHV), Japanese encephalitis virus (JEV), Murray Valley encephalitis virus (MVEV), Alfuy virus, Rocio virus (ROCV), St. Louis encephalitis virus (SLEV), Usutu virus (USUV), West Nile virus (WNV), Yaounde virus (YAOV)

Kokobera Virus Group:

Kokobera virus (KOKV)

Ntaya virus group: Bagaza virus (BAGV), Baiyangdian virus (BYDV), Duck egg drop syndrome virus (BYDV), Ilheus virus (ILHV), Jiangsu virus (JSV), Israel turkey meningoencephalomyelitis virus (ITV), Ntaya virus (NTAV), Tembusu virus (TMUV), Spondweni virus group, Zika virus (ZIKV), Yellow fever virus group, Banzi virus (BANV), Bouboui virus (BOUV), Edge Hill virus (EHV), Jugra virus (JUGV), Saboya virus (SABV), Sepik virus (SEPV), Uganda S virus (UGSV), Wesselsbron virus (WESSV) and Yellow fever virus (YFV)

Entebbe Virus Group:

Entebbe bat virus (ENTV), Yokose virus (YOKV)

Modoc Virus Group:

Apoi virus (APOIV), Cowbone Ridge virus (CRV), Jutiapa virus (JUTV), Modoc virus (MODV), Sal Vieja virus (SVV) and San Perlita virus (SPV)

Rio Bravo Virus Group:

Bukalasa bat virus (BBV), Carey Island virus (CIV), Dakar bat virus (DBV), Montana myotis leukoencephalitis virus (MMLV), Phnom Penh bat virus (PPBV) and Rio Bravo virus (RBV).

According to one embodiment, the virus is one of the four serotypes that cause Dengue fever (dengue virus type 1, dengue virus type 2, dengue virus type 3, and dengue virus type 4).

Nucleic acid sequences of the DNA sequence encoding the genome of the wild-type dengue virus type 1 are provided in SEQ ID NOs: 1-652.

Nucleic acid sequences of the DNA sequence encoding the genome of the wild-type dengue virus type 2 are provided in SEQ ID NOs: 653-1268.

Nucleic acid sequences of the DNA sequence encoding the genome of the wild-type dengue virus type 3 are provided in SEQ ID NOs: 1269-1625.

Nucleic acid sequences of the DNA sequence encoding the genome of the wild-type dengue virus type 4 are provided in SEQ ID NOs: 1626-1670.

In certain non-limiting embodiments of the present invention, the virus is poliovirus (PV), rhinovirus, influenza virus including avian flu (e.g. H5N1 subtype of influenza A virus), severe acute respiratory syndrome (SARS) coronavirus, Human Immunodeficiency Virus (HIV), Hepatitis B Virus (HBV), Hepatitis C Virus (HCV), infectious bronchitis virus, ebolavirus, Marburg virus, dengue fever virus (Flavivirus serotypes), West Nile disease virus, Epstein-Barr virus (EBV), yellow fever virus, Ebola (ebolavirus), chickenpox (varicella-zoster virus), measles (a paramyxovirus), mumps (a paramyxovirus), rabies (Lyssavirus), human papillomavirus, Kaposi's sarcoma-associated herpesvirus, Herpes Simplex Virus (HSV Type 1), or genital herpes (HSV Type 2). Other examples of viruses contemplated by the present invention are those disclosed in WO 2008121992, the contents of which are incorporated herein by reference.

In various embodiments, the attenuated virus belongs to the delta virus family and all related genera.

In various embodiments, the attenuated virus belongs to the Adenoviridae virus family and all related genera, strains, types and isolates for example but not limited to human adenovirus A, B, C.

In various embodiments, the attenuated virus belongs to the Herpesviridae virus family and all related genera, strains, types and isolates for example but not limited to herpes simplex virus.

In various embodiments, the attenuated virus belongs to the Reoviridae virus family and all related genera, strains, types and isolates.

In various embodiments, the attenuated virus belongs to the Papillomaviridae virus family and all related genera, strains, types and isolates.

In various embodiments, the attenuated virus belongs to the Poxviridae virus family and all related genera, strains, types and isolates.

In various embodiments, the attenuated virus belongs to the Retroviridae virus family and all related genera, strains, types and isolates. For example, but not limited to Human Immunodeficiency Virus.

In various embodiments, the attenuated virus belongs to the Filoviridae virus family and all related genera, strains, types and isolates.

In various embodiments, the attenuated virus belongs to the Paramyxoviridae virus family and all related genera, strains, types and isolates.

In various embodiments, the attenuated virus belongs to the Orthomyxoviridae virus family and all related genera, strains, types and isolates.

In various embodiments, the attenuated virus belongs to the Picornaviridae virus family and all related genera, strains, types and isolates.

In various embodiments, the attenuated virus belongs to the Bunyaviridae virus family and all related genera, strains, types and isolates.

In various embodiments, the attenuated virus belongs to the Nidovirales virus family and all related genera, strains, types and isolates.

In various embodiments, the attenuated virus belongs to the Caliciviridae virus family and all related genera, strains, types and isolates.

In other embodiments, the attenuated virus may be used as a non-pathogenic viral vectors for plant transformation.

The virulent virus (from which the attenuated virus is directly or non-directly derived) may be a "wild type" or "naturally occurring" prototype or isolate of variants. However, parent viruses also include mutants specifically created or selected in the laboratory on the basis of real or perceived desirable properties. Accordingly, parent viruses that are candidates for attenuation include mutants of wild type or naturally occurring viruses that have deletions, insertions, amino acid substitutions and the like, and also include mutants which have codon substitutions. In one embodiment, such a parent sequence differs from a natural isolate by about 30 amino acids or fewer. In another embodiment, the parent sequence differs from a natural isolate by about 20 amino acids or fewer. In yet another embodiment, the parent sequence differs from a natural isolate by about 10 amino acids or fewer.

As used herein, the term "attenuated virus" refers to a virus, in which the virulence thereof has been reduced, e.g. by genetic manipulation of the viral genome.

In one embodiment, the attenuated virus is a live virus.

In another embodiment, the attenuated virus is a dead e.g. killed virus (i.e. not capable of replication).

Preferably, the virulence of the virus has been reduced by at least 5 fold, 10 fold or even greater. Viral attenuation can be confirmed in ways that are well known to one of ordinary skill in the art Non-limiting, examples induce plaque assays, growth measurements, and reduced lethality in test animals.

The attenuation of the virus pertains to its virulence (pathogenicity), but does not necessarily affect the replicative capability of a virus. An attenuated virus can still be capable of replication. Thus, it may be a strain of a virus whose pathogenicity has been reduced so that it will initiate the immune response without causing the specific disease.

As mentioned, an RNA (or a DNA which transcribes to the RNA) of the attenuated virus of this aspect of the present invention is genetically modified such that there is a change in folding energy (e.g. local folding energy) or structure of the RNA of the protein encoding region thereof at positions which have been shown to display evolutionarily conserved RNA structure.

According to this aspect of the present invention, the phrase "evolutionarily conserved structure" refers to a structure/or lack thereof, being present in at least 10%, 20%, 30%, 40%, 50%, 60%, 70%, 80%, 90%, 91%, 92%, 93%, 94%, 95%, 96%, 97%, 98%, 99% or 100% of the known serotypes, genotypes, strains, variants or isolates of a particular virus. Specifically, the % of the strain can be chosen such that the signal will be statistically significant based on an appropriate null model.

In one embodiment, the evolutionarily conserved RNA structure refers to a general secondary structure and not to a specific structure per se.

In another embodiment, the evolutionarily conserved RNA structure refers to the presence of a particular structure (e.g. a hairpin structure, a stem and/or a loop).

In another embodiment, the evolutionarily conserved RNA structure refers to the absence of a secondary structure.

It will be appreciated that when there is a change in structure, there may or may not be a change in folding energy. However, when there is a change in folding energy, this is typically always associated with a change of structure.

Preferably, the RNA (or DNA encoding same) is modified at protein-coding bases. In one embodiment, only the protein-coding bases are modified such that the untranslated region of the RNA is identical to the untranslated region of the corresponding RNA of the virulent virus.

The modifications contemplated by the present inventors may be any modification that results in a reduction of virulence of the virus, including for example substitutions, insertions and deletions. The modifications may be synonymous or non-synonymous.

According to one embodiment, the modification is such that the amino acid sequence of the protein encoded by the RNA is at least 95% identical to the amino acid sequence of the protein of the wild-type, virulent virus.

According to one embodiment, the modification is such that the amino acid sequence of the protein encoded by the RNA is at least 96% identical to the amino acid sequence of the protein of the wild-type, virulent virus.

According to another embodiment, the modification is such that the amino acid sequence of the protein encoded by the RNA is at least 97% identical to the amino acid sequence of the protein of the wild-type, virulent virus.

According to yet another embodiment, the modification is such that the amino acid sequence of the protein encoded by the RNA is at least 98% identical to the amino acid sequence of the protein of the wild-type, virulent virus.

According to still another embodiment, the modification is such that the amino acid sequence of the protein encoded by the RNA is at least 99% identical to the amino acid sequence of the protein of the wild-type, virulent virus.

According to another embodiment, the modification is such that the amino acid sequence of the protein encoded by the RNA is 100% identical to the amino acid sequence of the protein of the wild-type, virulent virus.

Preferably the RNA of the attenuated virus is less than 90%, 85%, 80%, 75% or even 70% identical to the corresponding RNA of the virulent virus.

In one embodiment, the proteins encoded by the modified attenuated virus differ from the wild-type (virulent) virus by about 20 amino acids, 10 amino acids, five amino acids or fewer.

In one embodiment, the modification results in a conservation substitution in the encoded protein of the RNA.

The term "conservative substitution" as used herein, refers to the replacement of an amino acid present in the native sequence of the protein with a naturally occurring amino acid having similar steric properties. Where the side-chain of the native amino acid to be replaced is either polar or hydrophobic, the conservative substitution should be with a naturally occurring amino acid which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

When affecting conservative substitutions the substituting amino acid should have the same or a similar functional group in the side chain as the original amino acid.

In another embodiment, the modification results in a non-conservation substitution in the encoded protein of the RNA.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a protein that induces an immunogenic response in a subject but does not cause virulence.

According to a particular embodiment, the substitution is a synonymous substitution—i.e. the substitution of at least one base for another in a region of the RNA which codes for a protein, such that the amino acid sequence of the translated protein is not modified.

"Synonymous" codons are codons that encode the same amino acid. Thus, for example, CUU, CUC, CUA, CUG, UUA, and UUG are synonymous codons that code for Leucine (Leu). Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy. Thus, to replace a given codon in a nucleic acid by a synonymous but less frequently used codon is to substitute a "deoptimized" (in terms of speed) codon into the nucleic acid.

In one embodiment, the codons of the RNA are replaced with synonymous codons while maintaining the overall codon bias of the virus. Thus, the overall the average number of rare and/or frequent codons remains the same throughout the RNA.

In another embodiment, the codons of the RNA are replaced with synonymous codons thereby altering the overall codon bias of the virus. Thus, the overall average number of rare and/or frequent codons differs from the wild-type virulent virus.

As used herein, a "rare" codon refers to one of at least two synonymous codons encoding a particular amino acid that is present in an mRNA at a significantly lower frequency than the most frequently used codon for that amino acid. Thus, the rare codon may be present for example at about a 2-fold lower frequency than the most frequently used codon. in one embodiment, the rare codon is present at least a 3-fold, more preferably at least a 5-fold, lower frequency than the most frequently used codon for the amino acid. Conversely, a "frequent" codon refers to one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid.

In one embodiment, the codons of the RNA are replaced with synonymous codons while maintaining codon pair bias of the virus. In another embodiment, the codons of the RNA are replaced with synonymous codons thereby altering the overall codon pair bias of the virus. Codon pair virus is described in WO 2008121992, the contents of which are incorporated herein by reference.

Synonymous codons are provided in Table 1 herein below. The first nucleotide in each codon encoding a particular amino acid is shown in the left-most column; the second nucleotide is shown in the top row; and the third nucleotide is shown in the right-most column.

TABLE 1

| | Genetic Code | | | | |
|---|---|---|---|---|---|
| | U | C | A | G | |
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

As mentioned, the virus is modified so as to change the folding energy or structure of the RNA at positions of evolutionarily conserved structure.

The folding energy (FE) is a thermodynamic energy involved in maintaining a secondary structure available to perform physical work while being released, and thus is characterized by non-positive values. mRNA secondary structure is believed to be in the most stable conformation when a minimum amount of free folding energy is exerted (the FE obtains the most negative value). The number and strength of hydrogen bonds in RNA determine the folding energy, which is related to the folding strength of the structure: more negative FE indicates possibly stronger and more stable folding, while less negative FE corresponds to weaker and less structured conformations.

According to one embodiment, a position with weak RNA folding (less negative free energy/higher free energy) is modified to increase the RNA folding thereof (i.e. make the free energy more negative). Positions of weak folding may be defined based on a comparison to a random model that can maintain various basic properties/features of the viral genome (for example, the amino acid content/order, the codon frequencies, the di-nucleotide frequencies, or any combination of these properties/features). If the probability to see weaker folding in this position in the corresponding random genomes is lower than a certain threshold (e.g. 0.05, 0.01, 0.005, 0.001, 0.0001, 0.00001, 0.000001 or the largest p-value that pass correction for multiple hypothesis testing) the position may be defined as a position with weak folding.

According to one embodiment, a position with strong RNA folding (more negative free energy/lower free energy) is modified to decrease the RNA folding thereof (i.e. make the free energy less negative). Positions of strong folding may be defined based on a comparison to a random model that can maintain various basic properties/features of the viral genome (for example, the amino acid content/order, the codon frequencies, the di-nucleotide frequencies, or any combination of these properties/features). If the probability to see stronger folding in this position in the corresponding random genomes is lower than a certain threshold (e.g. 0.05, 0.01, 0.005, 0.001, 0.0001, 0.00001, 0.000001 or the largest p-value that pass correction for multiple hypothesis testing) the position may be defined as a position with strong folding.

For example, the following are the folding energies (average over all genomes considering 5 nt neighborhood around the location) and locations (the index of the nucleotide relatively to the 5' end/beginning of the genome) of positions with significant (p-values=0.001 and higher than maximal value observed in randomized genomes) weak/strong folding energy in the case of the second DNGV serotype (serotype 2):

Locations:

| 8893 | 8894 | 8895 | 2163 | 2164 | 8892 | 2162 | 8896 | 9808 | 9807 | 9806 | 2165 |
|---|---|---|---|---|---|---|---|---|---|---|---|
| | 9805 | 9809 | 8897 | 2161 | 9810 | 8891 | 8898 | 9804 | 8899 | 9718 | 9717 |
| | 7304 | 9811 | 8890 | 7305 | 9716 | 2166 | 9719 | 8900 | 9715 | 9714 | 9713 |
| | 9812 | 8889 | 2160 | 9720 | 9712 | 9803 | 6838 | 6837 | 9711 | 7303 | 8888 |
| | 6836 | 9710 | 9721 | 7306 | 8917 | 8916 | 8915 | 9709 | 6839 | 2167 | 8914 |
| | 9722 | 6835 | 9813 | 9708 | 2159 | 9802 | 9707 | 8918 | 9723 | 6840 | 6834 |
| | 9706 | 8913 | 9814 | 9724 | 1457 | 1458 | 9705 | 2168 | 2158 | 1456 | 6833 |
| | 7307 | 8919 | 6841 | 8092 | 543 | 9801 | 542 | 7302 | 7818 | 9725 | 541 |
| | 8091 | 1459 | 9815 | 7817 | 551 | 9734 | 9733 | 9698 | 550 | 7819 | 9697 |
| | 9732 | 9699 | 540 | 7816 | 9735 | 9975 | 1455 | 9700 | 6832 | 7820 | 9974 |
| | 1460 | 9731 | 9701 | 1372 | 552 | 9696 | 9726 | 9736 | 7815 | 1373 | 6842 |
| | 1454 | 7821 | 7238 | 8912 | 8093 | 1371 | 9816 | 9695 | 9730 | 3886 | 9737 |
| | 3887 | 7814 | 1447 | 3885 | 3889 | 3888 | 3890 | 3891 | 3892 | 539 | 9800 |
| | 5092 | 3893 | 7237 | 9727 | 9973 | 9694 | 8090 | 8920 | 7822 | 9278 | 3884 |
| | 2169 | 9738 | 553 | 9279 | 9729 | 2157 | 9277 | 9280 | 3894 | 7899 | 7898 |
| | 9728 | 5093 | 7897 | 7895 | 7896 | 9693 | 7893 | 7892 | 1374 | 7891 | 1362 |
| | 1441 | 1442 | 1446 | 1461 | 9739 | 1440 | 9276 | 7890 | 9692 | 7239 | 9740 |
| | 1361 | 701 | 5094 | 3883 | 1439 | 9281 | 403 | 7301 | 392 | 393 | 394 |
| | 402 | 404 | 7639 | 405 | 9817 | 1443 | 391 | 1370 | 7236 | 7638 | 1363 |
| | 9972 | 7308 | 1445 | 9691 | 7694 | 7637 | 7889 | 9275 | 8094 | 3895 | 538 |
| | 7695 | 7636 | 700 | 1472 | 2179 | 2181 | 2180 | 7635 | 2182 | 1473 | 7634 | have evolutionary selection for strong folding. In all of them the folding free energy is between −15 and −9.

Locations:

| 554 | 390 | 5095 | 2178 | 406 | 7633 | 7631 | 7632 | 1444 | 7630 | 8089 | 1464 |
|---|---|---|---|---|---|---|---|---|---|---|---|
| | 1360 | 9818 | 3882 | 1375 | 7240 | 6823 | 1438 | 1465 | 8921 | 3268 | 2183 |
| | 1474 | 5161 | 699 | 5160 | 7696 | 2265 | 8911 | 5162 | 7629 | 1466 | 9690 |
| | 9274 | 9971 | 3357 | 1364 | 3267 | 2177 | 407 | 1467 | 5159 | 5096 | 9819 |
| | 7888 | 7235 | 2184 | 1674 | 1675 | 1676 | 389 | 3581 | 1677 | 1437 | 1588 |
| | 4037 | 4036 | 1589 | 1673 | 3580 | 3582 | 3358 | 6822 | 1436 | 4458 | 1435 |
| | 2641 | 3579 | 7697 | 449 | 1475 | 1434 | 3578 | 305 | 1369 | 2642 | 3577 |
| | 4035 | 4459 | 5163 | 537 | 7628 | 3896 | 4457 | 3266 | 3881 | 304 | 1468 |
| | 1587 | 2176 | 1672 | 1590 | 2266 | 3576 | 3583 | 4038 | 7309 | 3359 | 1359 |
| | 2640 | 7241 | 9820 | 8095 | 3360 | 1469 | 5198 | 555 | 2616 | 4449 | 698 |
| | 1591 | 4039 | 2185 | 1671 | 1181 | 4034 | 1182 | 9821 | 5199 | 4450 | 306 |
| | 3265 | 4460 | 5197 | 448 | 5158 | 4456 | 3361 | 9689 | 1180 | 9822 | 1678 |
| | 9273 | 1365 | 2175 | 408 | 8088 | 7627 | 1476 | 9911 | 8134 | 2615 | 4448 |
| | 4451 | 9910 | 3264 | 3575 | 303 | 3353 | 2617 | 7355 | 8135 | 1670 | 9909 |
| | 8133 | 2643 | 388 | 5164 | 2267 | 3584 | 8136 | 7698 | 9791 | 7398 | 7399 |
| | 9908 | 1047 | 8922 | 3880 | 6821 | 1183 | 7234 | 5200 | 4033 | 9912 | 1048 |
| | 5951 | 5952 | 1586 | 7887 | 1432 | 7354 | 8137 | 2186 | 8132 | 2639 | 9823 |
| | 6092 | 1049 | 6091 | 7400 | 1669 | 9988 | 9987 | 4461 | 4125 | 9998 | 3263 |
| | 9986 | 1179 | 2618 | 6090 | 1679 | 5196 | 1050 | 6089 | 6961 | 3574 | 1358 |
| | 2174 | 6962 | 1043 | 119 | 7356 | 7397 | 9790 | 3362 | 5165 | 4126 | 307 |
| | 5950 | 9907 | 3585 | 1042 | 3897 | 2268 | 4447 | 2365 | 409 | 7353 | 1051 | have evolutionary selection for strong folding. In all of them the folding free energy is between −9 and −8.

Locations:

| 3879 | 1041 | 1668 | 697 | 1978 | 536 | 2249 | 4032 | 7626 | 5953 | 7401 | 9989 |
|---|---|---|---|---|---|---|---|---|---|---|---|
| | 6963 | 9913 | 7242 | 1528 | 5157 | 1184 | 1052 | 1585 | 1529 | 2366 | 2248 |
| | 1530 | 4127 | 2644 | 8247 | 1667 | 1386 | 8910 | 5949 | 8131 | 8246 | 447 |
| | 2250 | 1040 | 9824 | 4201 | 6093 | 1053 | 9688 | 2619 | 9906 | 423 | 9997 |
| | 387 | 302 | 8245 | 2187 | 1977 | 4200 | 9914 | 3352 | 6964 | 3573 | 2638 |
| | 1054 | 1431 | 2367 | 4128 | 3419 | 424 | 1666 | 4202 | 1680 | 426 | 4130 |

-continued

| | | | | | | | | | | |
|---|---|---|---|---|---|---|---|---|---|---|
| | 9789 | 5195 | 4129 | 9915 | 1039 | 425 | 556 | 9990 | 9905 | 9996 | 1357 |
| | 7352 | 5166 | 5579 | 5580 | 4203 | 6820 | 9916 | 268 | 1976 | 3420 | 2629 |
| | 3586 | 3484 | 1531 | 7233 | 1356 | 2630 | 5954 | 5578 | 4692 | 6965 | 2247 |
| | 267 | 9825 | 3485 | 2269 | 5581 | 4462 | 9917 | 2628 | 1355 | 1038 | 308 |
| | 3483 | 7357 | 8244 | 8130 | 1354 | 4693 | 7886 | 9995 | 2620 | 2631 | 1527 |
| | 495 | 1353 | 2368 | 8248 | 3486 | 2364 | 9918 | 427 | 3482 | 2627 | 6246 |
| | 5577 | 494 | 1665 | 3572 | 4691 | 7396 | 1975 | 3481 | 410 | 120 | 2626 |
| | 9991 | 8715 | 266 | 5582 | 9919 | 3487 | 4204 | 6094 | 1681 | 496 | 9904 |
| | 1387 | 4694 | 9994 | 9992 | 9920 | 9788 | 7625 | 2625 | 1037 | 3587 | 5576 |
| | 5156 | 428 | 3351 | 696 | 301 | 2246 | 7358 | 1430 | 5194 | 8129 | 9993 |
| | 7405 | 3488 | 6247 | 1532 | 4463 | 535 | 2624 | 4690 | 309 | 9921 | 2621 |
| | 1974 | 9687 | 411 | 493 | 5356 | 2623 | 8716 | 429 | 1526 | 5358 | 1664 |
| | 5357 | 8714 | 2622 | 6245 | 6344 | 6112 | 6113 | 1682 | 6111 | 5583 | 7359 |
| | 446 | 820 | 557 | 6114 | 6743 | 1683 | 281 | 6110 | 3489 | 2363 | 8249 |
| | 4464 | 5955 | 6742 | 821 | 430 | 5359 | 822 | 823 | 3345 | 1684 | 2369 | have evolutionary selection for strong folding. In all of them
the folding free energy is between −7 and −6.
Locations:

| | | | | | | | | | | |
|---|---|---|---|---|---|---|---|---|---|---|
| 9781 | 9903 | 8360 | 1388 | 6819 | 824 | 5965 | 2245 | 3346 | 6095 | 3350 | 277 |
| | 497 | 280 | 6724 | 4205 | 6115 | 278 | 1429 | 6744 | 1036 | 7395 | 3347 |
| | 534 | 9787 | 8361 | 6248 | 9613 | 7624 | 279 | 276 | 6741 | 4689 | 8713 |
| | 3344 | 1522 | 8909 | 1663 | 3348 | 533 | 272 | 300 | 3349 | 2003 | 2004 |
| | 6343 | 1973 | 2005 | 2006 | 275 | 6725 | 8717 | 4875 | 4465 | 8362 | 121 |
| | 2002 | 8250 | 2761 | 492 | 825 | 4876 | 273 | 6244 | 1428 | 532 | 2362 |
| | 5155 | 3490 | 9612 | 2007 | 531 | 5360 | 274 | 6726 | 3343 | 5964 | 695 |
| | 3849 | 7386 | 558 | 565 | 7387 | 1691 | 2760 | 9782 | 7385 | 2244 | 8363 |
| | 5956 | 1095 | 564 | 9902 | 1692 | 6727 | 9484 | 6740 | 1389 | 9485 | 2991 |
| | 8251 | 2992 | 9786 | 566 | 1098 | 563 | 6730 | 8364 | 1662 | 6729 | 9611 |
| | 4688 | 4206 | 6096 | 5963 | 7623 | 2008 | 6728 | 3342 | 1521 | 3848 | 4466 |
| | 1693 | 1225 | 498 | 559 | 8712 | 445 | 7394 | 2759 | 2993 | 2361 | 6818 |
| | 1536 | 1972 | 562 | 8718 | 6249 | 5957 | 5962 | 6342 | 3491 | 5958 | 8252 |
| | 5361 | 4415 | 9783 | 2846 | 8255 | 560 | 567 | 6731 | 5961 | 8253 | 1035 |
| | 8254 | 1226 | 9483 | 3847 | 8256 | 561 | 2845 | 8908 | 3341 | 9785 | 2843 |
| | 2844 | 2936 | 826 | 4467 | 1694 | 8723 | 1390 | 2994 | 9784 | 4687 | 8257 |
| | 2848 | 2842 | 9610 | 491 | 9901 | 2758 | 8724 | 1227 | 1405 | 2360 | 7152 |
| | 3340 | 4414 | 2849 | 6243 | 6732 | 8722 | 4468 | 8725 | 2757 | 8719 | 8263 |
| | 3338 | 8258 | 3339 | 3845 | 3492 | 8264 | 568 | 8711 | 499 | 2850 | 7153 |
| | 1228 | 2841 | 6097 | 5154 | 4469 | 1971 | 4686 | 2756 | 1964 | 2935 | 3337 |
| | 9482 | 6739 | 8265 | 4470 | 1406 | 8259 | 3794 | 1695 | 2753 | 2851 | 8721 |

40 have evolutionary selection for strong folding. In all of them
the folding free energy is between −6 and −5.
Locations:

| | | | | | | | | | | |
|---|---|---|---|---|---|---|---|---|---|---|
| 2754 | 6341 | 2840 | 4471 | 4207 | 3493 | 2755 | 4413 | 6250 | 2852 | 2752 | 2853 |
| | 8266 | 4487 | 4472 | 6098 | 1537 | 3500 | 2854 | 3499 | 3498 | 8262 | 8260 |
| | 7154 | 827 | 3336 | 8720 | 500 | 3497 | 2839 | 3501 | 569 | 1965 | 4350 |
| | 2855 | 1034 | 9481 | 3496 | 2751 | 3495 | 4473 | 1407 | 3494 | 4486 | 1970 |
| | 490 | 9609 | 1966 | 3335 | 2856 | 2750 | 2715 | 8267 | 6099 | 2934 | 5153 |
| | 6340 | 1967 | 503 | 504 | 4485 | 2714 | 4412 | 501 | 1408 | 6242 | 7155 |
| | 4351 | 570 | 2027 | 502 | 2028 | 2711 | 2029 | 2710 | 2709 | 2026 | 2706 |
| | 2857 | 2713 | 3793 | 2708 | 3334 | 4474 | 2705 | 1968 | 2712 | 2702 | 489 |
| | 2707 | 828 | 2704 | 4208 | 1010 | 2749 | 2030 | 1969 | 1409 | 6100 | 2703 |
| | 4352 | 1538 | 2933 | 2701 | 2690 | 7156 | 2858 | 488 | 571 | 4353 | 3333 |
| | 2691 | 4484 | 2700 | 9608 | 2031 | 2748 | 2689 | 6101 | 5152 | 2747 | 2932 |
| | 2699 | 4411 | 4475 | 4354 | 2567 | 2568 | 2698 | 4355 | 2692 | 1011 | 2569 |
| | 2733 | 7157 | 4356 | 2566 | 2570 | 2859 | 2032 | 2693 | 2571 | 2572 | 6102 |
| | 2734 | 4483 | 2565 | 2742 | 1012 | 2573 | 4209 | 2738 | 2737 | 2697 | 2741 |
| | 2564 | 4357 | 2740 | 2694 | 2345 | 2536 | 7158 | 2574 | 2348 | 2739 | 5151 |
| | 2736 | 2563 | 4410 | 4476 | 1013 | 2349 | 2735 | 2347 | 1539 | 1287 | 2696 |
| | 2575 | 9607 | 4482 | 7213 | 2695 | 2346 | 2523 | 2033 | 2576 | 7212 | 1014 |
| | 2535 | 4358 | 4210 | 4477 | 1021 | 4481 | 1015 | 2524 | 7211 | 2577 | 2534 |
| | 1288 | 4478 | 1016 | 2525 | 4480 | 4479 | 2034 | 9606 | 2533 | 1020 | 2578 |
| | 7210 | 2526 | 2532 | 1017 | 2579 | 3977 | 2531 | 3975 | 3976 | 3978 | 1019 |
| | 2530 | 2529 | 2528 | 2527 | 2580 | 1018 | 7209 | 3979 | 7208 | 7207 | | have evolutionary selection for strong folding. In all of them the folding free energy is between −5 and −0.5.
Locations:

| | | | | | | | | | | |
|---|---|---|---|---|---|---|---|---|---|---|
| 554 | 555 | 8434 | 5349 | 4054 | 6354 | 4055 | 7347 | 4053 | 5350 | 8433 | 5348 |
| | 4056 | 536 | 4061 | 6942 | 4062 | 5351 | 4063 | 6538 | 4064 | 4060 | 4052 |
| | 4065 | 6943 | 4059 | 8432 | 9184 | 4057 | 4058 | 6353 | 6941 | 556 | 8431 |
| | 6949 | 6950 | 6944 | 109 | 6948 | 7348 | 5352 | 6352 | 6947 | 2247 | 6946 |
| | 3262 | 6945 | 6951 | 4051 | 6351 | 6940 | 5347 | 6350 | 2889 | 6952 | 6539 |
| | 6953 | 10043 | 10044 | 8430 | 334 | 6954 | 5042 | 4050 | 10042 | 2246 | |
| | 10041 | 535 | 333 | 335 | 7349 | 10040 | 10045 | 9416 | 4049 | 446 | |
| | 10046 | 557 | 6939 | 8429 | 3261 | 8424 | 332 | 1102 | 2888 | 5315 | 6546 |
| | 5041 | 7350 | 2245 | 6545 | 8234 | 8425 | 1101 | 8428 | 534 | 8595 | 108 |
| | 6547 | 6540 | 5504 | 336 | 6544 | 8427 | 533 | 8426 | 9417 | 5314 | 3006 |
| | 530 | 9649 | 5505 | 9183 | 9650 | 8235 | 3007 | 9648 | 5781 | 1100 | 6686 |
| | 7266 | 3005 | 6938 | 532 | 9651 | 531 | 8236 | 3850 | 3849 | 2887 | 558 |
| | 5639 | 5506 | 6548 | 2244 | 3851 | 9454 | 564 | 9484 | 9485 | 8485 | 9647 |
| | 96 | 6500 | 9634 | 867 | 5635 | 3569 | 5040 | 6543 | 4514 | 1098 | 4515 |
| | 563 | 1099 | 9486 | 8237 | 4513 | 3852 | 8935 | 3063 | 3848 | 5507 | 3004 |
| | 559 | 5638 | 5313 | 6776 | 5636 | 6541 | 445 | 8230 | 4516 | 9455 | 3009 |
| | 868 | 5637 | 6557 | 7260 | 2243 | 562 | 3260 | 2242 | 6777 | 6937 | 9652 |
| | 3564 | 107 | 337 | 2886 | 6936 | 4512 | 2241 | 4517 | 7800 | 9864 | 6775 |
| | 3860 | 7125 | 2240 | 9646 | 560 | 7801 | 3394 | 9418 | 6556 | 9483 | 3847 |
| | 7430 | 6549 | 561 | 869 | 5782 | 2239 | 4518 | 3568 | 627 | 6542 | 7429 |
| | 5508 | 7431 | 1263 | 6935 | 7267 | 7063 | 5336 | 7928 | | | | have evolutionary selection for weak folding. In all of them the folding free energy is between −9 and −5.
Locations

| | | | | | | | | | | |
|---|---|---|---|---|---|---|---|---|---|---|
| 1264 | 6550 | 9456 | 6555 | 6491 | 3393 | 6499 | 8940 | 9635 | 7802 | 97 | 2238 |
| | 6492 | 7428 | 642 | 6778 | 3003 | 9645 | 6490 | 7432 | 2885 | 4519 | 6551 |
| | 441 | 7427 | 4511 | 3859 | 3846 | 5509 | 4768 | 7152 | 5337 | 7929 | 2232 |
| | 6554 | 7124 | 1265 | 3854 | 5312 | 3010 | 6774 | 9642 | 6552 | 3062 | 6553 |
| | 8486 | 7806 | 444 | 9637 | 9638 | 4767 | 7803 | 3845 | 6489 | 9636 | 7151 |
| | 3855 | 3858 | 3844 | 2237 | 7123 | 9644 | 5510 | 8520 | 7153 | 9653 | 3567 |
| | 6934 | 7930 | 8936 | 6493 | 2233 | 1796 | 3565 | 3392 | 9643 | 8770 | 7150 |
| | 7062 | 6488 | 4520 | 3856 | 5887 | 9482 | 7804 | 871 | 106 | 2234 | 3857 |
| | 4766 | 4510 | 442 | 9459 | 8939 | 9419 | 5467 | 8521 | 1266 | 2236 | 2127 |
| | 6487 | 5039 | 7122 | 7119 | 7931 | 443 | 4471 | 5888 | 8229 | 2235 | 4207 |
| | 7961 | 338 | 5511 | 7149 | 8526 | 6498 | 7120 | 98 | 6765 | 3002 | 7121 |
| | 3566 | 7805 | 9460 | 5311 | 872 | 8525 | 4472 | 7118 | 4509 | 5783 | 6494 |
| | 7117 | 3391 | 7010 | 6766 | 5889 | 4521 | 7154 | 7673 | 3011 | 6764 | 9461 |
| | 7268 | 3378 | 2998 | 7061 | 8522 | 8527 | 9182 | 4582 | 9462 | 9463 | 9464 |
| | 9465 | 9481 | 5468 | 6779 | 7932 | 6685 | 873 | 2126 | 8937 | 1519 | 1267 |
| | 349 | 8938 | 1617 | 5512 | 1924 | 3390 | 348 | 4508 | 9420 | 6773 | 5890 |
| | 9668 | 4473 | 7148 | 5248 | 9654 | 7116 | 7259 | 9667 | 9863 | 4765 | 9666 |
| | 4587 | 1618 | 9466 | 8524 | 3001 | 5469 | 8785 | 5310 | 4499 | 2999 | 8487 |
| | 7674 | 3259 | 628 | 4247 | 8523 | 6767 | 9665 | 9664 | 7975 | 99 | 4507 |
| | 9362 | 3389 | 5891 | 7933 | 1619 | 5470 | 641 | 4246 | 7105 | 5519 | 5892 |
| | 1881 | 4506 | 1880 | 7962 | 7974 | 6497 | | | | | | have evolutionary selection for weak folding. In all of them the folding free energy is between −5 and −4.
Locations:

| | | | | | | | | | | |
|---|---|---|---|---|---|---|---|---|---|---|
| 1879 | 5893 | 350 | 4522 | 9663 | 7060 | 1620 | 9421 | 5308 | 4248 | 8786 | 4586 |
| | 6495 | 4585 | 6772 | 7147 | 1622 | 3000 | 9489 | 5518 | 5894 | 1795 | 5309 |
| | 9480 | 3379 | 8792 | 4505 | 1621 | 8769 | 5520 | 5513 | 2125 | 5895 | 9467 |
| | 1882 | 7973 | 6780 | 4583 | 6771 | 4500 | 4584 | 5896 | 3388 | 4249 | 6770 |
| | 7968 | 6768 | 7972 | 6769 | 339 | 6496 | 104 | 7969 | 5521 | 7675 | 5522 |
| | 7146 | 5517 | 1883 | 8787 | 3258 | 7970 | 3012 | 1623 | 4504 | 7967 | 7971 |
| | 630 | 7059 | 4250 | 5516 | 9599 | 7269 | 5897 | 100 | 8791 | 4764 | 7011 |
| | 5471 | 9655 | 629 | 7056 | 7057 | 7058 | 4245 | 4474 | 7115 | 5038 | 6199 |
| | 1884 | 7104 | 4523 | 103 | 4501 | 3387 | 5514 | 3017 | 351 | 7966 | 4208 |
| | 7963 | 347 | 8228 | 101 | 9479 | 4251 | 7934 | 7055 | 102 | 9662 | 4502 |
| | 8788 | 5515 | 1885 | 4503 | 6781 | 6198 | 8790 | 9509 | 5249 | 9850 | 2025 |
| | 1624 | 7965 | 8789 | 5853 | 2124 | 7145 | 9490 | 7054 | 9852 | 4524 | 3016 |
| | 7680 | 9851 | 5898 | 7964 | 7746 | 6197 | 7096 | 2374 | 6782 | 7270 | 3386 |
| | 9468 | 7114 | 9508 | 7258 | 1923 | 5854 | 9064 | 9065 | 3380 | 9067 | 9066 |
| | 352 | 4525 | 1517 | 4244 | 7676 | 631 | 595 | 2024 | 9068 | 7255 | 9063 |
| | 1625 | 1516 | 9862 | 6911 | 3015 | 9507 | 5784 | 9069 | 9070 | 9661 | 9853 |
| | 6910 | 9478 | 3013 | 6912 | 9506 | 6930 | 4475 | 640 | 9062 | 7679 | 8768 |

-continued

| | | | | | | | | | | |
|---|---|---|---|---|---|---|---|---|---|---|
| 3014 | 7935 | 8488 | 9071 | 5855 | 9656 | 9181 | 340 | 9600 | 6913 | 3385 |
| 7012 | 3282 | 7053 | 9061 | 9854 | 633 | 632 | 1333 | 7113 | 6196 | 3381 |
| 5899 | 7678 | 9171 | 6919 | 9263 | 7018 | 1794 | 5037 | 9072 | 6914 | 9491 |
| 2023 | 589 | 194 | 6918 | 6915 | 1711 | | | | | | have evolutionary selection for weak folding. In all of them the folding free energy is between −4 and −3.
Locations:

| | | | | | | | | | | |
|---|---|---|---|---|---|---|---|---|---|---|
| 346 | 6920 | 5250 | 1712 | 7019 | 2123 | 7017 | 1626 | 6916 | 1715 | 3384 | 1713 |
| | 1714 | 6665 | 3382 | 8762 | 1334 | 6917 | 3383 | 9073 | 1716 | 590 | 7677 |
| | 6929 | 9660 | 9657 | 7097 | 7020 | 9469 | 6783 | 9855 | 7257 | 6921 | 1710 |
| | 7256 | 4209 | 7103 | 9477 | 201 | 2375 | 2388 | 1335 | 7747 | 5856 | 1708 |
| | 7021 | 1337 | 7112 | 9659 | 594 | 1705 | 7016 | 574 | 786 | 1707 | 1709 |
| | 2022 | 9172 | 1336 | 9658 | 7936 | 4476 | 7013 | 4644 | 584 | 7022 | 9492 |
| | 583 | 6922 | 9861 | 341 | 1147 | 2219 | 1706 | 10136 | 10135 | 7111 | 1627 |
| | 6928 | 193 | 10134 | 593 | 1728 | 4643 | 10133 | 6143 | 9856 | 6142 | 4213 |
| | 10137 | 7023 | 10132 | 9262 | 5900 | 6141 | 591 | 4642 | 7052 | 8226 | 634 |
| | 6140 | 10139 | 6144 | 7015 | 9601 | 8767 | 1922 | 9476 | 10131 | 6195 | 7024 |
| | 2033 | 1628 | 588 | 1123 | 4641 | 10138 | 10130 | 8494 | 2387 | 7025 | 592 |
| | 8763 | 1729 | 9493 | 2021 | 575 | 4362 | 785 | 1629 | 7026 | 6923 | |
| | 10140 | 7027 | 5251 | 585 | 6139 | 7028 | 9180 | 9470 | 202 | 7029 | 1146 |
| | 586 | 186 | 7098 | 345 | 4358 | 6784 | 9173 | 6927 | 4210 | 587 | 1730 |
| | 5857 | 3283 | 7014 | 3722 | 6138 | 4640 | 9860 | 582 | 639 | 2020 | 342 |
| | 9859 | 9858 | 4212 | 3721 | 5785 | 9857 | 9475 | 1511 | 10141 | 8489 | 192 |
| | 187 | 8764 | 784 | 6924 | 2225 | 4361 | 4635 | 2376 | 4359 | 1731 | 8766 |
| | 4638 | 7748 | 1145 | 3720 | 576 | 2220 | 2386 | 4360 | 6926 | 4639 | 8765 |
| | 8225 | 10142 | 5901 | 188 | 9261 | 7030 | 2042 | 2221 | 372 | 3719 | 203 |
| | 10143 | 6925 | 4637 | 6664 | 1793 | 9179 | 1733 | 2041 | 1732 | 9474 | 191 |
| | 344 | 9471 | 2224 | 1734 | 3718 | 9174 | 7102 | | | | | have evolutionary selection for weak folding. In all of them the folding free energy is between −3 and −2.
Locations

| | | | | | | | | | | |
|---|---|---|---|---|---|---|---|---|---|---|
| 1510 | 4636 | 8046 | 8045 | 4211 | 5252 | 343 | 190 | 189 | 2222 | 8490 | 7051 |
| | 1735 | 2034 | 5858 | 9602 | 9606 | 783 | 2377 | 2223 | 8047 | 638 | 9473 |
| | 1144 | 8493 | 637 | 636 | 2040 | 6785 | 7099 | 635 | 8044 | 8039 | 8038 |
| | 1736 | 9178 | 9472 | 782 | 5786 | 8037 | 8040 | 2385 | 8491 | 5255 | 577 |
| | 581 | 9177 | 5253 | 10144 | 1124 | 1143 | 5902 | 1142 | 8043 | 8041 | 7031 |
| | 3284 | 368 | 1737 | 2378 | 5254 | 781 | 8042 | 8492 | 7749 | 8224 | 2379 |
| | 5905 | 2039 | 9260 | 3717 | 9176 | 2380 | 1921 | 2381 | 1141 | 9255 | 8048 |
| | 2382 | 9175 | 1738 | 9256 | 2383 | 2384 | 1509 | 8294 | 5787 | 9257 | 2821 |
| | 9254 | 5903 | 2035 | 5904 | 9258 | 5859 | 9259 | 9253 | 5788 | 8295 | 7101 |
| | 2038 | 7750 | 371 | 9605 | 6786 | 7032 | 369 | 7050 | 9252 | 9603 | 578 |
| | 9243 | 2820 | 9251 | 1140 | 8223 | 9604 | 8296 | 7100 | 2817 | 1508 | 9242 |
| | 7751 | 2036 | 9250 | 580 | 1125 | 9244 | 1775 | 1776 | 8297 | 1792 | 1777 |
| | 8049 | 2819 | 2818 | 9241 | 1774 | 2037 | 8298 | 9249 | 8299 | 6663 | 9240 |
| | 9245 | 1507 | 8300 | 5860 | 1506 | 9232 | 9233 | 9234 | 9231 | 9248 | 8301 |
| | 9235 | 9247 | 9239 | 9236 | 9230 | 7033 | 1139 | 1773 | 9246 | 1126 | 8302 |
| | 9229 | 9237 | 5861 | 579 | 1920 | 8222 | 9238 | 7049 | 1791 | 1127 | 1906 |
| | 1905 | 1907 | 1908 | 1772 | 1909 | 1128 | 1910 | 8050 | 1129 | 1911 | 1912 |
| | 1913 | 1130 | 1138 | 1918 | 1919 | 1917 | 1914 | 1916 | 1915 | 1771 | 1790 |
| | 7048 | 7034 | 1131 | 7047 | 1770 | 7035 | 1132 | 6662 | 7046 | 1137 | 7036 |
| | 7045 | 1769 | 1133 | 7044 | 7043 | 7037 | 7042 | 7041 | 1134 | 7040 | 1136 |
| | 7039 | 7038 | 6661 | 1135 | | | | | | | | have evolutionary selection for weak folding. In all of them the folding free energy is between −2 and −0.2.

According to a particular embodiment, the folding energy refers to a local folding energy (e.g. in genomic windows of between 20-100 nucleotides, 30-90 nucleotides, 30-80 nucleotides, 30-70 nucleotides, 30-60 nucleotides, 30-50 nucleotides, 30-40 nucleotides).

The genetic modifications (e.g. synonymous codon substitutions) may be engineered in locations undergoing conserved evolutionary selection for strong or weak folding distributed throughout the genome, or in multiple locations restricted to a portion of the genome e.g. in a region which encodes one, two, three, four or more particular proteins. In one embodiment, the genetic modifications (synonymous codon substitutions) are effected throughout an RNA (or DNA transcribable to same) which encodes a polypeptide.

In one embodiment, the modifications are effected over a length of at least about 500 nucleotides, 1000 nucleotides, 5000 nucleotides or more.

In further embodiments, the portion of the genome encoding the capsid coding region is modified so as to alter the evolutionarily conserved structure of the RNA.

Preferably, the modifications (e.g. synonymous codon substitutions) are effected such that at least 3, 5, 10, 15, 20, 25, 30, 35, 40, 45, 50, 100, 150, 200, 250, 300, 350, 400, 450, 500 local sites of evolutionarily conserved structure are altered, for example 3-500, 10-50, 20-400, 20-300, 20-200.

In another embodiment, the modifications (e.g. synonymous codon substitutions) are effected such that at least 0.1% 0.5%, 1%, 2%, 3%, 4%, 5%, 6%, 7%, 8%, 9%, 10% of the viral genome is altered.

According to another embodiment, the modifications (e.g. synonymous codon substitutions) are effected such that the increase in folding energy at at least one location of evolutionarily conserved structure (i.e. undergoing an evolutionary selection for strong folding) is greater than 9 kcal/mol, more preferably greater than 9.5 kcal/mol, and even more preferably greater than 10 kcal/mol, and best preferably about 12 kcal/mol.

According to another embodiment, the modifications (e.g. synonymous codon substitutions) are effected such that the decrease in folding energy at at least one location of evolutionarily conserved non-structure (i.e. undergoing an evolutionary selection for weak folding) is greater than 20 kcal/mol, more preferably greater than 22 kcal/mol, and even more preferably greater than 25 kcal/mol, and best preferably 25 kcal/mol.

According to another embodiment, the modifications (e.g. synonymous codon substitutions) are effected such that the increase in folding energy at least 20% of the locations of evolutionarily conserved structure (i.e. undergoing an evolutionary selection for strong folding) is greater than 7 kcal/mol, more preferably greater than 8 kcal/mol, and even more preferably greater than 10 kcal/mol, and best preferably about 12 kcal/mol.

According to another embodiment, the modifications (e.g. synonymous codon substitutions) are effected such that the decrease in folding energy at at least 20% of the locations of evolutionarily conserved non-structure (i.e. undergoing an evolutionary selection for weak folding) is greater than 17 kcal/mol, more preferably greater than 19 kcal/mol, and even more preferably greater than 21 kcal/mol, and best preferably 23 kcal/mol.

According to another embodiment, the modifications (e.g. synonymous codon substitutions) are effected such that the increase in folding energy at at least 30% of the locations of evolutionarily conserved structure (i.e. undergoing an evolutionary selection for strong folding) is greater than 6 kcal/mol, more preferably greater than 8 kcal/mol, and even more preferably greater than 9 kcal/mol, and best preferably 11 kcal/mol.

According to another embodiment, the modifications (e.g. synonymous codon substitutions) are effected such that the decrease in folding energy at at least 30% of the locations of evolutionarily conserved non-structure (i.e. undergoing an evolutionary selection for weak folding) is greater than 16 kcal/mol, more preferably greater than 18 kcal/mol, and even more preferably greater than 20 kcal/mol, and best preferably 22 kcal/mol.

According to another embodiment, the modifications (e.g. synonymous codon substitutions) are effected such that the increase in folding energy at at least 40% of the locations of evolutionarily conserved structure (i.e. undergoing an evolutionary selection for strong folding) is greater than 6 kcal/mol, more preferably greater than 8 kcal/mol, and even more preferably greater than 9 kcal/mol, and best preferably 10 kcal/mol.

According to another embodiment, the modifications (e.g. synonymous codon substitutions) are effected such that the decrease in folding energy at at least 40% of the locations of evolutionarily conserved non-structure (i.e. undergoing an evolutionary selection for weak folding) is greater than 15 kcal/mol, more preferably greater than 17 kcal/mol, and even more preferably greater than 20 kcal/mol, and best preferably 22 kcal/mol.

According to another embodiment, the modifications (e.g. synonymous codon substitutions) are effected such that the increase in folding energy at at least 50% of the locations of evolutionarily conserved structure (i.e. undergoing an evolutionary selection for strong folding) is greater than 6 kcal/mol, more preferably greater than 7 kcal/mol, and even more preferably greater than 9 kcal/mol, and best preferably 10 kcal/mol.

According to another embodiment, the modifications (e.g. synonymous codon substitutions) are effected such that the decrease in folding energy at at least 50% of the locations of evolutionarily conserved non-structure (i.e. undergoing an evolutionary selection for weak folding) is greater than 14 kcal/mol, more preferably greater than 17 kcal/mol, and even more preferably greater than 19 kcal/mol, and best preferably 22 kcal/mol.

According to another embodiment, the modifications (e.g. synonymous codon substitutions) are effected such that the increase in folding energy at at least 60% of the locations of evolutionarily conserved structure (i.e. undergoing an evolutionary selection for strong folding) is greater than 5 kcal/mol, more preferably greater than 7 kcal/mol, and even more preferably greater than 8 kcal/mol, and best preferably 10 kcal/mol.

According to another embodiment, the modifications (e.g. synonymous codon substitutions) are effected such that the decrease in folding energy at at least 60% of the locations of evolutionarily conserved non-structure (i.e. undergoing an evolutionary selection for weak folding) is greater than 14 kcal/mol, more preferably greater than 16, and even more preferably greater than 19 kcal/mol, and best preferably 21 kcal/mol.

According to another embodiment, the modifications (e.g. synonymous codon substitutions) are effected such that the increase in folding energy at at least 70% of the locations of evolutionarily conserved structure (i.e. undergoing an evolutionary selection for strong folding) is greater than 5 kcal/mol, more preferably greater than 6 kcal/mol, and even more preferably greater than 8 kcal/mol, and best preferably 10 kcal/mol.

According to another embodiment, the modifications (e.g. synonymous codon substitutions) are effected such that the decrease in folding energy at at least 70% of the locations of evolutionarily conserved non-structure (i.e. undergoing an evolutionary selection for weak folding) is greater than 13 kcal/mol, more preferably greater than 16 kcal/mol, and even more preferably greater than 18 kcal/mol, and best preferably 21 kcal/mol.

According to another embodiment, the modifications (e.g. synonymous codon substitutions) are effected such that the increase in folding energy at at least 80% of the locations of evolutionarily conserved structure (i.e. undergoing an evolutionary selection for strong folding) is greater than 4 kcal/mol, more preferably greater than 6 kcal/mol, and even more preferably greater than 8 kcal/mol, and best preferably 10 kcal/mol.

According to another embodiment, the modifications (e.g. synonymous codon substitutions) are effected such that decrease in folding energy at at least 80% of the locations of evolutionarily conserved non-structure (i.e. undergoing an evolutionary selection for weak folding) is greater than 12 kcal/mol, more preferably greater than 15 kcal/mol, and even more preferably greater than 18 kcal/mol, and best preferably 21 kcal/mol.

According to another embodiment, the modifications (e.g. synonymous codon substitutions) are effected such that the increase in folding energy at at least 90% of the locations of evolutionarily conserved structure (i.e. undergoing an evolutionary selection for strong folding) is greater than 4 kcal/mol, more preferably greater than 6 kcal/mol, and even more preferably greater than 8 kcal/mol, and best preferably 10 kcal/mol.

According to another embodiment, the modifications (e.g. synonymous codon substitutions) are effected such that the decrease in folding energy at at least 90% of the locations of evolutionarily conserved non-structure (i.e. undergoing an evolutionary selection for weak folding) is greater than 10 kcal/mol, more preferably greater than 14 kcal/mol, and even more preferably greater than 18 kcal/mol, and best preferably 21 kcal/mol.

According to another embodiment, the modifications (e.g. synonymous codon substitutions) are effected such that the increase in folding energy at least 95% of the locations of evolutionarily conserved structure (i.e. undergoing an evolutionary selection for strong folding) is greater than 3 kcal/mol, more preferably greater than 5 kcal/mol, and even more preferably greater than 8 kcal/mol, and best preferably 10 kcal/mol.

According to another embodiment, the modifications (e.g. synonymous codon substitutions) are effected such that the decrease in folding energy at least 95% of the locations of evolutionarily conserved non-structure (i.e. undergoing an evolutionary selection for weak folding) is greater than 10 kcal/mol, more preferably greater than 14 kcal/mol, and even more preferably greater than 18 kcal/mol, and best preferably 22 kcal/mol.

According to another embodiment, the modifications (e.g. synonymous codon substitutions) are effected such that the increase in folding energy at 100% of the locations of evolutionarily conserved structure (i.e. undergoing an evolutionary selection for strong folding) is greater than 3 kcal/mol, more preferably greater than 5 kcal/mol, and even more preferably greater than 8 kcal/mol, and best preferably 10 kcal/mol.

According to another embodiment, the modifications (e.g. synonymous codon substitutions) are effected such that the decrease in folding energy at 100% of the locations of evolutionarily conserved non-structure (i.e. undergoing an evolutionary selection for weak folding) is greater than 9 kcal/mol, more preferably greater than 13 kcal/mol, and even more preferably greater than 18 kcal/mol, and best preferably 22 kcal/mol.

In one embodiment, identifying evolutionarily conserved local structure of viral RNA can be carried out as described herein below.

Essentially, nucleic acid sequences of viruses are collected. Such sequences may be available from known databases and/or generated by sequencing viral genomes.

Next, the sequences are aligned. According to a particular embodiment, the viral nucleic acid sequences are computationally translated to the corresponding amino-acid chains which are then mutually aligned. The aligned amino-acid sequences are back translated to the corresponding nucleotide sequences basing on the original nucleotide composition of each genome.

The sequence multiple alignment can be followed by additional procedures, which may potentially improve the robustness and/or the computational efficiency of the subsequent stages of the method. In some embodiments, these procedures may include:

(1) Selection of N most diverse samples from the aligned sequences, when the diversity between two aligned sequences can be measured by the Hamming distance or other appropriate metrics (see Algorithm 1, in the examples section herein below).

(2) Filtration of possibly corrupted sequences, by selecting only those which have up-to K % of positions occupied by indels/ambiguous symbols.

In some embodiments, the numbers N and K are 100 and 5 correspondingly, while in others, they may take any suitable value. Moreover, other embodiments may also include additional preprocessing steps depending on the underlying data and/or any additional constraints.

In the next step, genome randomization is performed. For each sequence, N randomized variants are created. In some embodiments the number N is 20, 50 100 or 200 while in others, or any other suitable value. The randomized variants are restricted to maintain the amino acid sequence, and thus the protein structure, by sampling (with or without repetition) from the set of synonymous codons for each amino acid position. In conjunction, additional constraints may be employed.

In one embodiment two randomization models that consider the codon distribution are used:

HCUB: this randomization/null model maintains the distribution of codons (and the amino acid content) in each genome separately; specifically, each codon in the randomized genome is sampled according to the distribution (frequency) of codons coding the same amino acid in the wild-type genome (see Algorithm 2, in the examples section herein below).

VCUB: this randomization/null model maintains the synonymous codon distribution in each column in the multiple alignment matrix, thus, maintaining the column wise composition of amino acids and the distribution of synonymous codons (and thus nucleotides), but not for each genome separately/horizontally. This is achieved by permuting synonymous codons in each column. In the case of multiple amino acids in a column, each amino acid is permuted separately; thus, obtaining for each amino acid the same codon frequencies as in the original alignment matrix (but in a different order) (see Algorithm 3, in the examples section herein below).

In other words, both random models are based on marginal distributions of synonymous codons encoded in the alignment matrix, but while the HCUB uses the ('horizontal') distributions of synonymous codons defined by the matrix rows, VCUB uses the ('vertical') distributions defined by matrix columns.

In other embodiments randomization models based on additional biologically-motivated constraints may be employed (e.g. constraints on GC content, distribution of dinucleotides).

Construction of Local Genomic Features Profiles:

Local Genomic Features: Local genomic features (LGF) are defined by the compositions of nucleotides that comprise local regions of a genomic sequence. In addition to being responsible for the content of the genetic products directly encoded by the sequence, these compositions may carry additional important regulatory characteristics playing a crucial role in all stages of the viral gene expression. Examples of local genomic features may include among others: measures of nucleotide bias (e.g., distribution of k-mers of nucleotides, GC content); measures of codon usage bias (e.g., distribution of k-mers of codons, transfer RNA and codon adaptation indexes, effective number of codons), sequence regulatory patterns (e.g., order and clustering of codons, Kozak/Shine-Dalgarno-like features, initiation context scores), structural features (e.g., amino-acid charge, folding energy, secondary structure), etc. All these features, are encoded in the genomic sequences (ORFs and UTRs), and may contribute to viral replication regulation and may (at least partially) evolve via synonymous mutations that do not affect the amino acid composition of the encoded protein.

Local Genomic Features Profiles: Profiles of local genomic features are constructed by applying a sliding window of length N with a step S to a genomic sequence. At each step a specific genomic feature of a local genomic region enclosed by the window is calculated, resulting in a LGF profile $$F=[F_1, \ldots, F_j, F_{i+m}, \ldots, F_k],$$

where $F_j$ is the value of a LGF corresponding to the window starting at position j.

In one embodiment, profiles of local folding energies in all 39 nt genomic windows (LGF=folding energy, N=39, S=1) are computed. In other embodiments different values of window size (10-100, 20-90, 30-80, 30-70, 30-60, 30-50) and step, and/or different local genomic features may be used. In some embodiments profiles corresponding to more than one genomic feature may be constructed.

Identification of Single-Sequence Salient Local Regions

A single-sequence evolutionary salient local region is defined to be a local genomic region, corresponding to a position in a profile, in which the corresponding LGF value is statistically significant (based on a comparison to a certain random models). Such regions are possibly under an evolutionary pressure on the corresponding feature (i.e., undergo a positive/negative evolutionary selection). As their name suggests, single-sequence evolutionary salient regions are identified for each sequences separately.

The statistical significance is estimates via a p-value with respect to one or several null model based on randomized genomic variants (see stage 3 above). In general, Monte Carlo methods, based on N randomized variants, provide an empirical p-value estimate, rather than an exact measure, of the real p-value. This empirical approximation has two direct consequences. First, the resolution of the resultant p-values is restricted to 1/N; second, the smallest achievable p-value is 1/N. This means that a very large number of samples is required to accurately estimate a small p-value. In general, more than N samples are required to reliably estimate a p-value of 1/N. Low resolution p-values may limit the applicability of the False Discovery Rate (FDR) correction, which is necessary to prevent large numbers of false positives in a multiple testing framework. On the other hand, the empirical approximation may overestimate p-values that are, in reality, smaller.

These considerations, justify extending the empirical p-value by extrapolating the null model distribution to account for more extreme values.

In one embodiment, to identify single-sequence evolutionary salient local regions a wild-type LGF profile is compared with a matrix of LGF profiles based on randomized variants (each row in the matrix corresponds to one randomized variant). The comparison is performed in a position dependent manner (each position in the wild type profile is compared to the corresponding column in the matrix of randomized profiles) as follows: for each position the one-sample Kolmogorov-Smirnov test (KST) is used to check the null hypothesis whether the sample of random variables given by the corresponding column in the matrix of randomized variants is drawn from a Normal distribution. If the null hypothesis is accepted, the p-value is approximated analytically by the one sided analytical p-value coming from the corresponding Normal distribution with sample mean and sample standard deviation parameters. Otherwise, an empirical p-value is estimated by calculating the portion of the randomized values as extreme as in the wild type (see Algorithm 4, in the examples section herein below).

Positions with empirical p-value<1/N, in which the null hypothesis of KST was not accepted, may be farther, re-estimated using a higher number of randomized variants (leading to a higher resolution empirical p-value).

Local regions corresponding to positions having statistically significant (p-value<1/N) LGF values that pass the False Discovery Rate (FDR) filtering are defined to be single-sequence evolutionary salient local regions.

Identification of Multi Sequence Evolutionary Salient Local Regions:

In some embodiments, it may be required to identify salient genomic regions by analyzing conjointly single-sequence evolutionary salient local regions identified in different sequences.

This analysis is based on a N×L binary Selection Matrix $$S = \begin{bmatrix} \delta_{11} & \cdots & \delta_{1k} \\ \vdots & \ddots & \vdots \\ \delta_{N1} & \cdots & \delta_{Nk} \end{bmatrix},$$

$$\delta_{ij} = \begin{cases} 1, & \text{position } j \text{ is salient in profile } i \\ 0, & \text{otherwise} \end{cases}$$

where N is the number of different sequences and L is a corresponding LGF profile length.

The selection matrix is used to construct second-order LGF profiles—profiles that are based on local statistics of single-sequence evolutionary salient local regions identified in different LGF profiles.

The multi-sequence evolutionary salient local regions are defined to be regions corresponding to statistically significant positions in second-order LGF profiles; these regions are mutually salient in all or part of the analyzed sequences.

In one embodiment the multi-sequence salient local regions may be based on the following second-order LGF profiles:

LGF Selection Concentration Profiles

Selection Concentration Profiles are computed by applying a W-nt long sliding window (termed the SCI-interval) on all LGF profiles: in each step the Selection Concentration Index (SCI), defined as the average (over all sequences) number of single-sequence evolutionary salient local regions inside the corresponding window, is calculated (see Algorithm 5, in the examples section herein below). Selection Concentration Profiles characterize the distribution of single-sequence evolutionary salient local regions along the genomes.

In one embodiment the number W is 100, while in others, they may take any suitable value.

SCI-intervals with significantly high selection concentration (significantly high SCI values) are identified by comparing the wild type SCI values in each position to the SCI values from the corresponding positions in the randomized selection concentration profiles generated according to the following algorithm, named One-Versus-Rest (OVR) random model: in each randomized LGF profile, the single-sequence evolutionary salient local regions are identified by comparing it to the rest of the randomized LGF profiles from the same wild-type origin; the obtained salient regions are then used to construct randomized selection concentration profiles (see Algorithm 6, in the examples section herein below), which serve as a baseline (null-model) for an empirical p-value computation (see Algorithm 7, in the examples section herein below). Statistically significant SCI-intervals are named Concentration Intervals (in terms of single-sequence evolutionary salient local regions; see FIGS. 6A-B).

LGF Selection Preservation Profiles

Due to genetic variability on the one hand, and possible inaccuracies in sequencing and multiple alignment on the other, single-sequence evolutionary salient local regions in different genomes may be shifted one with respect to the other. To account for these possible displacements when quantifying the levels of selection preservation, we defined the Selection Preservation Index (SPI) as the percentage of different aligned genomes which have at least one significant position inside a W-nt length genomic interval (termed by us the SPI-interval). In one embodiment, the number W is 25, while in others, they may take any suitable value.

The SPI takes a range of values between 0 and 1: the higher the value—the more different sequences have single-sequence evolutionary salient local regions inside the corresponding SPI-interval (a higher selection preservation), the lower—the less single-sequence evolutionary salient local regions are shared (a lower selection preservation). The Selection Preservation Profiles are calculated by applying a W-nt sliding window to the aligned LGF profiles of all or part of the sequences, and calculating at each step the corresponding SPI value.

SPI-intervals with significantly high selection preservation (significantly high SPI values) are identified by comparing the wild type SPI values in each position to the SPI values from the corresponding positions in the randomized selection preservation profiles generated according to the OVR random model (see the description above and/or Algorithm 7).

In one embodiment SPI-intervals with selection preservation index higher than in 1000 corresponding randomized variants (p-value<0.001; Benjamini-Hochberg FDR=0.001) were chosen; those of them which achieved SPI values higher than maximally achieved SPI in randomized variants were defined as statistically significant SPI-intervals and named Preserved Intervals (in terms of selection preservation in single-sequence salient local regions).

Clusters of Preserved/Concentration Intervals

The resulting Preserved/Concentration are not independent: parts of them belong to intersecting genomic regions and could be possibly attributed to the same or partially-overlapping elements. Therefore, in some embodiments, clusters of concentration intervals/preserved intervals may be computed. A cluster consists of all Preserved/Concentration intervals, such that the distance between the 5' ends of two consecutive intervals in a cluster is no more than D nucleotides.

Selection Concentration and Selection Preservation profiles are considered as second-order LGF profiles; Concentration intervals/Preserved intervals are considered as multi-sequence evolutionary salient local regions.

Sampling of the most significant salient local regions.

In some embodiments, a set of N identified single/multi-sequence evolutionary salient local regions is sub-sampled for K<N most significant regions according to additional rules.

In some embodiments, intersection of regions, mutually salient with respect to some portion of different randomization models, or across different genotypic groups (e.g. serotypes) may be selected.

In other embodiments, single/multi-sequence evolutionary salient local regions identified with respect to each one of the different randomization models (and/or genotypic groups) separately may be ranked individually according to some significance measure (e.g. p-value, z-score); the obtained rank lists are than aggregated and a mutual short list of top K regions is chosen (see Algorithm 8, in the examples section herein below).

The K most significant salient regions may be further sparsified, e.g. by identifying cluster of salient regions and choosing one/several representative of each cluster.

Once the positions of evolutionarily conserved RNA secondary structure are identified, the regions are optimized/deoptimized with respect to the relevant LGF and/or other target functions. Modified sequences (or parts of sequences), based on mutations in one/several salient regions, comprise a potentially live attenuated virus.

In one embodiment the mutations are performed by substituting each codon with its least frequent synonym in the corresponding position in the multiple alignments; i.e. a codon that is not preferred by evolution.

In other embodiments salient regions, selected with respect to a specific LGF may be modified to maximize (minimize) the LGF value: if there is a statistical evidence (based on the randomized model) that in a certain position evolution shape LGF to have a maximal/high value the region may be mutated to decrease the LGF value as much as possible; similarly, if there is a statistical evidence (based on the randomized model) that in a certain position evolution shape LGF to have a minimal/low value the region may be mutated to increase the LGF value as much as possible.

For example, the present invention contemplates maximizing/minimizing local folding energy by changing codon usage while maintaining the encoded protein and possibly other constraints (e.g. the codon usage bias, GC content, etc). Local regions that are inferred to be under evolutionary section to have strong/weak folding according to a randomized model(s) may be manipulated to have weak/strong local folding strength respectively (i.e. the folding strength may be "deoptimized" in the opposite direction). This can be done without affecting the encoded protein(s) or any other feature of the viral genome via a brute force over all possible variants or an optimization algorithm, such as Simulated Annealing (Algorithm 9 and FIG. 7). The resulting sequence with manipulated local regions may be referred to as a folding-deoptimized sequence.

Using the above described methods the present inventors have uncovered potential polynucleotide sequences for Dengue viral genomes. DNA sequences encoding same are presented in SEQ ID NOs: 1671-1734. It will be appreciated that the present inventors contemplate sequences which are at least 80%, 85%, 90%, 91%, 92%, 93%, 94%, 95%, 96%, 97%, 98% and 99%, homologous to said sequences.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in an electronic device having digital computer capabilities arranged to run the computer program on the tangible medium or execute the instruction on a computer readable medium.

Computer programs implementing the method according to some embodiments of this invention can commonly be distributed to users on a distribution medium such as, but not limited to, CD-ROM, flash memory devices, flash drives, or, in some embodiments, drives accessible by means of network communication, over the internet (e.g., within a cloud environment), or over a cellular network. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. Computer programs implementing the method according to some embodiments of this invention can also be executed by one or more data processors that belong to a cloud computing environment. All these operations are well-known to those skilled in the art of computer systems. Data used and/or provided by the method of the present embodiments can be transmitted by means of network communication, over the internet, over a cellular network or over any type of network, suitable for data transmission.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

There are various computer programs which can be used to analyze the secondary structure of RNA (i.e. the folding energy profile). According to a particular embodiment, the computer program is Vienna (v. 2.1.9) package RNAfold function with default parameters. This function predicts the minimum free energy and the associated secondary structure for the input RNA sequence using a dynamic programming based on the thermodynamic nearest-neighbor approach (the Zucker algorithm. Other computer programs which may be used to predict secondary structure include but are not limited to CentroidFold, CentroidHomfold, Context Fold, CONTRAfold, CyloFold, IPknot, KineFold, Mfold, Pknots, PknotsRG, pKiss, RNA123, RNAshapes, RNA structure, SARNA-Predict, Sfold, UNAFold, Crumple and Slinking Windows and Assembly.

This invention further provides a method of synthesizing any of the attenuated viruses described herein, the method comprising modifying the codon usage of the protein encoding region of a genome of a virulent virus so as to encode an RNA having a sufficient change in folding energy at sites of evolutionarily conserved RNA structure so as to bring about attenuation of the viral genome.

In certain embodiments of the instant methods, the modifying is guided by computer-based algorithms that permit design of a viral genome by varying the codon usage such that there is a sufficient change in folding energy at localized sites of evolutionarily conserved RNA secondary structure so as to bring about attenuation of the viral genome.

Such computer-based algorithms select and exchange codons encoding the same amino acid at sites of evolutionarily conserved RNA secondary structure and computationally determines whether folding energy at the sites is changed by the exchanging.

According to some embodiments, the selecting and exchanging is repeated until the folding energy is changed by a maximum possible level per each position.

Additionally, or alternatively, the selecting and exchanging is repeated until the folding energy is changed by a maximum possible level at a predetermined number of positions (e.g. between 3 and 500, or up to 10% of the genome).

Generally, modifications are performed to a point at which the virus can still be grown in some cell lines (including lines specifically engineered to be permissive for a particular virus), but where the virus is avirulent in a normal animal or human. Such avirulent viruses are excellent candidates for either a killed or live vaccine since they encode exactly the same proteins as the fully virulent virus and accordingly provoke exactly the same immune response as the fully virulent virus. In addition, the process described herein offers the prospect for fine tuning the level of attenuation; that is, it provides the capacity to design synthetic viral genomes whose secondary structure is deoptimized to a roughly predictable extent. Design, synthesis, and production of viral particles is achievable in a timeframe of weeks once the genome sequence is known, which has important advantages for the production of vaccines in potential emergencies. Furthermore, the attenuated viruses are expected to have virtually no potential to revert to virulence because of the extremely large numbers of deleterious nucleotide changes involved. This method may be generally applicable to a wide range of viruses, requiring only knowledge of the viral genome sequence and a reverse genetics system for any particular virus.

Methods of modifying viral genomes are known in the art and employ molecular biology techniques such as in vitro transcription, reverse transcription, polymerase chain reaction, restriction digestion, cloning etc.

Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994).

When the viral genome is an RNA genome, they may be isolated from virions or from infected cells, converted to DNA ("cDNA") by the enzyme reverse transcriptase, possibly modified as desired, and reverted, usually via the RNA intermediate, back into infectious viral particles. Most commonly, the entire cDNA copy of the genome is cloned immediately downstream of a phage T7 RNA polymerase promoter that allows the in vitro synthesis of genome RNA, which is then transfected into cells for generation of virus (van der Wert, et al., 1986). Alternatively, the same DNA plasmid may be transfected into cells expressing the T7 RNA polymerase in the cytoplasm.

In certain embodiments the modifying is achieved by de novo synthesis of DNA containing the synonymous codons and substitution of the corresponding region of the genome with the synthesized DNA. In further embodiments, the entire genome is substituted with the synthesized DNA. In still further embodiments, a portion of the genome is substituted with the synthesized DNA.

The present invention provides a vaccine composition for inducing a protective immune response in a subject comprising any of the attenuated viruses described herein and a pharmaceutically acceptable carrier.

It should be understood that an attenuated virus of the invention, where used to elicit a protective immune response (i.e. immunize) in a subject or to prevent a subject from becoming afflicted with a virus-associated disease, is administered to the subject in the form of a composition additionally comprising a pharmaceutically acceptable carrier. Pharmaceutically acceptable carriers are well known to those skilled in the art and include, but are not limited to, one or more of 0.01-0. IM and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Pharmaceutically acceptable carriers can further comprise minor amounts of auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

This invention also provides a modified host cell line specially isolated or engineered to be permissive for an attenuated virus that is non-viable in a wild type host cell. Since the attenuated virus cannot grow in normal (wild type) host cells, it is absolutely dependent on the specific helper cell line for growth. This provides a very high level of safety for the generation of virus for vaccine production.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. "Exposed" to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, "administering" means delivering using any of the various methods and delivery systems known to those skilled in the art. Administering can be performed, for example, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

A "subject" refers to any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human polio virus receptor CD 155. In a preferred embodiment, the subject is a human. Preferred embodiments of birds are domesticated poultry species, including, but not limited to, chickens, turkeys, ducks, and geese.

A "prophylactically effective dose" is any amount of a vaccine that, when administered to a subject prone to viral infection or prone to affliction with a virus-associated disorder, induces in the subject an immune response that protects the subject from becoming infected by the virus or afflicted with the disorder. "Protecting" the subject means either reducing the likelihood of the subject's becoming infected with the virus, or lessening the likelihood of the disorder's onset in the subject, by at least two-fold, preferably at least tenfold. For example, if a subject has a 1% chance of becoming infected with a virus, a two-fold reduction in the likelihood of the subject becoming infected with the virus would result in the subject having a 0.5% chance of becoming infected with the virus. Most preferably, a "prophylactically effective dose" induces in the subject an immune response that completely prevents the subject from becoming infected by the virus or prevents the onset of the disorder in the subject entirely.

As used herein, a "therapeutically effective dose" is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An "adjuvant" shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21. [0182]. The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more poliovirus, one or more rhinovirus, one or more influenza virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range but also out of the range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al., (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Data preparation: 1,670 complete coding sequences of 4 DENVserotypes (651, 615, 356, 45 strains in serotypes 1-4 respectively) were downloaded.

We first translated the nucleotide coding regions and then aligned the resulting amino acid sequences by Clustal Omega package [2] with default parameters. To obtain the multiple alignment of corresponding nucleotide sequences we mapped the aligned amino acids back to the nucleotide sequences basing on the original nucleotide composition of each genome.

Genome randomization models: To investigate selection for folding energy, FE values were compared with corresponding sequence-randomized controls which preserve certain nonrandom features of the naturally occurring sequences. To exclude the possibility that the obtained signals were simply due to amino acid selection pressure (i.e., selection on the protein sequence), as opposed to selection for the folding strength, we restricted our randomized variants to maintain the amino acids order and content (and thus the encoded protein), by sampling from the set of synonymous codons for each amino acid position. To model evolutionary constraints (not necessary related to folding) imposed on synonymous variability in different genomic positions (e.g. mutational bias) we maintained the distribution of synonymous codons (and thus nucleotides) for each column in the interserotype multiple alignment matrix (matrix containing aligned sequences of 4 serotypes). This was achieved by random permutations of synonymous codons for each column in the alignment matrix; in the case of multiple amino acids in a column, each amino acid was permuted separately (FIG. 1B). In this way, for each amino acid the same 'vertical' codon frequencies as in the original alignment matrix (but in a different order) were obtained.

To model the composition of nucleotide pairs which are argued to have an important effect on formation of secondary structures, a model that preserves both the amino acids order and content, and the frequencies distribution of 16 possible pairs of adjacent nucleotides (dinucleotides) for each sequence separately was used. Although efficient methods exist for preserving the amino acids (e.g. permutation of synonymous codons) or the dinucleotides content (e.g. random generation of an Euler path in a De Bruijn-like graph, whose edges represent the dinucleotides [3]) separately, it has been difficult to combine them for satisfying both of the constraints. To overcome these difficulties, we used an elegant algorithm proposed in [4] which is based on a multivariate Boltzmann sampling scheme, initially introduced in the context of enumerative combinatorics. This algorithm produces random variants which feature both correct dinucleotide frequencies and coding capacity while being generated with provably uniform probability. We used the original source code which can be found in csb-dotcsdotmcgilldotca/sparcs.

For each one of 1,670 wild-type sequences, we computed 1,000 randomizations basing on each one of the randomization models, resulting in more than 3 million variants.

Local Folding Energy Profiles: Free folding energy (FE) is a thermodynamic energy involved in maintaining a secondary structure available to perform physical work while being released, and thus is characterized by non-positive values. mRNA secondary structure is believed to be in the most stable conformation when minimum amount of free energy is exerted (the FE obtains the most negative value). The local folding energy profiles (FE-profiles) were constructed by applying a 39 nt length sliding window to a genomic sequence (FIG. 1C): in each step the FE of a local subsequence enclosed by the corresponding window was calculated by Vienna (v. 2.1.9) package RNAfold function with default parameters [5]. This function predicts the minimum free energy and the associated secondary structure for the input RNA sequence using a dynamic programming based on the thermodynamic nearest-neighbor approach (the Zucker algorithm) [6-8].

Folding Energy Significance Test: In order to assess the statistical significance of the folding strength in a particular position in a sequence, we compared the FE values in this position with the FE values in the corresponding position in each one of the randomized variants by calculating an empiric p-value—a proportion of the randomized values as extreme as in the wild type. Positions with FE related $p\text{-value}<0.05$ were defined as having a "suspected" FE related signal; due to a high false discovery rate (Benjamini-Hochberg approach) of FE signals in individual sequences we went further and compared the positions of suspected signals across different genomes.

Conservation of local folding signals. Due to genetic variability on the one hand, and possible inaccuracies in sequencing and multiple alignment on the other, positions selected for a significant strong (weak) folding in different genomes may be shifted one with respect to the other. To account for these possible displacements when quantifying the conservation of FE related signals across different sequences, we defined a Signal Conservation Index (SCI) at a particular position as a percentage of different aligned sequences which have at least one signal inside a 5 nt length genomic neighborhood of this position (FIGS. 1C, E). SCI takes a range of values between 0 and 1: the higher the value—the more different sequences have FE related signals inside the corresponding neighborhood (higher signal conservation), the lower—the less sequences have FE related signals in common (lower signal conservation). A vector of SCI values in all positions along the coding regions (Signal Conservation Profile) was calculated by applying a 5 nt sliding window to the matrix of aligned FE-profiles (for each serotype and folding signal direction separately), and calculating at each step the corresponding signal conservation index.

Positions with significantly high FE related signal conservation were identified by comparing the wild type SCI values in each position to the SCI values from the corresponding positions in 1000 randomized signal conservation profiles (generated basing on suspected signals identified in 1000 randomized alignments via the OVR model). Those positions with significantly conserved signals (p-value<0.001 with respect to randomized selection conservation values, Benjamini-Hochberg false discovery rate=0.001) which had conservation levels higher than achieved in all corresponding randomized variants were defined as positions that undergo a conserved evolutionary selection for strong/weak folding (FE-selected positions).

The resulting positions are not independent: parts of them belong to intersecting genomic regions and could be possibly attributed to the same or partially-overlapping folding elements. Therefore we defined clusters of FE-selected positions; each cluster consists of all positions with significant signal conservation such that the distance between two consecutive positions in a cluster is no more than 44 nt. According to this definition positions within a particular cluster correspond to partially-overlapping genomic windows) 39 nt folding windows+5 nt offset used in signal conservation analysis); in contrast positions belonging to different clusters are thought as independent with respect to the performed local FE analysis.

We emphasize that conservation of FE related signals was analyzed for each serotype, and folding signal direction separately; specifically, in each case we accounted for positions selected for only one folding direction, either strong or weak. Moreover, the analysis of signal conservation was performed with respect to the evolutionary-constrained model only, since (in contrast to the dinucleotide-preservation or any other model based on a single sequence) it takes into consideration the co-evolution of viral variants and their phylogenetic dependencies.

One-Versus-Rest (OVR) Model: In order to estimate the expected number of suspected FE related signals (p-value<0.05) in random and in order to generate a null model for estimating the statistical significance of FE signal conservation in different positions, we simulated FE suspected signals in randomized variants according to the following procedure named One-Versus-Rest (OVR) model: for each one of the N randomized variants corresponding to a specific wild-type sequence, we identified iteratively its FE-related suspected signals with respect to the rest of the N−1 random variants (FIG. 1D). We then used the obtained sets of the randomized FE signals to construct the randomized signal conservation profiles: each randomized profile was generated by picking (without repetition) a single one-versus-rest randomized set of selected positions for each wild type sequence (resulting in a randomized alignment variant) and then applying the methodology for computing signal conservation levels as described above.

Normalized entropy as a measure for sequence variability. We defined the nucleotide/synonymous variability at a position i in the nucleotides/protein multiple alignment as Shannon entropy of a distribution on nucleotides/synonymous codons corresponding to the consensus amino acid, normalized by the maximal possible entropy value possible in the given position (this measure was also, independently, introduced, in [9]):

$$V_i = -\frac{\sum_{j=1}^{n} p_j \log_2(p_j)}{\log_2 n}$$

here n is the number of distinct elements in the corresponding alphabet; and $p_j$ are their relative frequencies (in the case of nucleotide variability, n=4, i.e. the number of different possible nucleotides; for synonymous variability n is the number of different synonymous codons corresponding to the consensus amino acid in this position).

This variability measure takes values between 0 and 1, and describes how dispersed the distribution of the alphabet elements is: higher values correspond to more uniform nucleotide/codon usage; lower values correspond to more biased nucleotide/codon usage, indicating that some nucleotides/synonymous codons are preferred.

The variability measure was computed for each serotype separately. The synonymous variability index was computed based on the consensus amino acid (the most frequent amino acid) in each position in the multiple alignments. In order to neutralize biases due to poor high number of indels and low consensus values (high amino acid variability), we filtered out positions with consensus levels of less than 90%, and number of gaps of more than 10% (resulting in ~4%, 6%, 3%, 3% filtered positions in serotypes 1-4 respectively). In addition, positions corresponding to singleton amino acids Methionine and Tryptophan (with a natural absence of variability) were excluded.

The variability profiles were constructed by applying a 44 nt sliding window along the alignment and averaging at each step the nucleotide/synonymous variability values at positions within the corresponding window. The window size was defined in a way that each such window matches the 39 nt genomic region in which the folding for the corresponding positions was predicted+a 5 nt allowed shift used in FE signals conservation analysis (FIG. 1C).

The z-score normalized synonymous variability was constructed by computing in each position a z-score with respect to 1000 variants based on randomized multiple alignments (each randomized alignment was constructed by taking a single, amino acids order preserving, random variant of each wild-type genome):

$$V_{z-score} = \frac{V - \mu}{\sigma}$$

($\mu/\sigma$—mean/s.t.d of randomized variability values at a particular position).

Software. Multiple alignments were performed with Clustal Omega package (v.1.2.0). Folding energies were predicted with RNAfold function from Vienna package (v.2.1.9) adapted by us to work with sliding windows. Other computations were performed using Matlab® software (MathWorks Inc.). For high performance computing, a Linux based cluster system was employed.

Results

The different general stages of the exemplified analyses appear in FIGS. 1A-E.

1,670 coding regions of different genomes from four DENV serotypes were downloaded and aligned (FIG. 1A I-II). For each coding region, reference sets of 1000 randomized variants that maintain some of the fundamental properties of the original sequences (FIG. 1A III) were generated.

To assess accurately the statistical significance of the predicted folding energies we employed a reference model that ensures that the reported results cannot be explained by the amino acid composition of the encoded proteins and/or the evolutionary, phylogenetically dependent pressure on synonymous codons along the coding regions (evolutionary-constrained model). To this aim, we designed randomized variants (a Null model) that preserved both the amino acids order of the wild type sequences and the column-wise frequencies of synonymous codons at each position along their alignment (FIG. 1B).

In addition, to make sure that the obtained folding signals were not mainly a consequence of disrupted stacking base-pairs we compared our results with a randomization model designed to maintain both the encoded protein and the distribution of frequencies of pairs of adjacent nucleotides (dinucleotides-constrained model).

Local folding energy profiles (FE-profiles) were computed for each wild-type and randomized sequence (FIGS. 1A IV, C).

To identify positions along the coding regions that were possibly selected during the course of viral evolution for significantly strong/weak folding (more/less negative FE), we investigated the position-wise statistical differences between the FE-profiles corresponding to the wild type sequences and FE-profiles of their randomized variants (FIG. 1A VI). For each sequence we considered the "suspected" positions for which the FE values were found to be lower/higher than in 5% of the corresponding randomized variants (i.e. positions with empiric FE associated p-value<0.05) and analyzed their tendency to maintain the folding related signals across different viral strains (FIGS. 1A VII, C, E); in addition the role of sequence variability in this phenomenon was investigated (FIG. 1A V).

To assess the expected number of suspected positions in randomized variants we designed the following procedure, named One-Versus-Rest (OVR) model: in each randomized FE-profile, the suspected folding related signals were identified by a position-wise comparison to the rest of the randomized FE-profiles from the same wild-type origin (FIG. 1D). Conceptually, the average number of randomized suspected positions (FE associated p-value<0.05) obtained in this procedure evaluates the expected number of false positive signals and therefore can serve for an empirical false discovery rate estimation.

In addition, the suspected positions identified in randomized variants (randomized suspected positions) were used to obtain a null model for FE signal conservation analysis.

Evidence that the DENV coding regions contain hundreds of positions that are likely to be selected for conserved strong or weak local folding structures. Folding energy was estimated in all genomic windows of length 39 nt (motivated by an approximated average ribosomal footprint [10] and in the order of magnitude of various intracellular complexes [11] and functional mRNA structures [12,13]) within the coding region of each viral genome, and the resulting values were used to construct local FE-profiles: each position in a profile contained a FE value computed in a window starting at this position.

FE-profile of each wild-type sequence was compared in a position-wise manner to the FE-profiles of the corresponding evolutionary-constrained randomized variants (randomized FE profiles); positions with p-value<0.05 were defined as "suspected" to have significantly more/less negative FE in comparison to random (i.e. carrying a "suspected" folding related signal).

During the second step, aiming at distinguishing signals that are due to mutation bias from signals that undergo an evolutionary selection, we went further to identify positions along the coding region which tend to maintain FE related signals in different viral variants. Such positions may belong to the same orthologous functional elements (i.e. elements conserved in various genomes with respect to their function but not necessarily conserved with respect to their sequence) and could have important implications for viral fitness.

To quantify the tendency of a particular position in the coding region to maintain a conserved signal, we computed the percentage of different sequences for which at least one suspected folding related signal was identified within a 5 nucleotides neighborhood of this position (FIGS. 1C, E). For convenience we termed this measure Signal Conservation Index (SCI). The SCI values range between 0 (none of the sequences have any local FE signal around the position) and 1 (100% of the sequences have a FE signal within the allowed neighborhood).

To assess the statistical significance of FE signal conservation, we compared the wild-type SCI values to a reference model based on 1000 randomized alignments in which selection conservation was computed with respect to the randomized suspected signals detected via the OVR procedure. As a result, we identified positions with a statistically significant FE signal conservation (SCI associated p-value<0.001; Benjamini-Hochberg false discovery rate 0.001); those of them with conservation levels higher than 0.20, 0.20, 0.21, 0.42 (thresholds which are equal to the maximal SCI values achieved in random in serotypes 1-4 correspondingly for both folding signal directions) were defined as positions that are likely to undergo a conserved evolutionary selection for strong/weak folding (shortly, FE-selected positions).

Profiles of SCI values along the coding regions are shown in FIG. 2A. Positions with a significantly conserved strong folding signal were found to constitute 53, 65, 62, 66 different clusters in serotypes 1-4 correspondingly; likewise, weak local folding signal was identified as conserved in positions grouped in 49, 73, 58, 65 clusters. Each cluster was comprised of positions with significantly conserved FE related signals predicted in intersecting 44 nt genomic windows (39 nt folding window size+5 nt allowed shift in signal position in conservation analysis); these positions could be possibly attributed to the same or partially-overlapping folding elements.

The resulting conservation levels were found to be spread over a wide range of values; specifically 20%-90% of FE-selected positions (depending on serotype and the direction of the folding signal) possessed SCI values greater than 0.5 (meaning that the FE related signals in these positions were maintained in more than 50% of the sequences); in 2%-7% of FE-selected positions the conservation levels where higher than 0.9 (meaning a conservation of the FE signal therein in more than 90% sequences; FIG. 2B).

The total amounts of FE-selected positions in all serotypes were found to be significantly higher (p-value<0.001; on average 40-100 folds, depending on serotype and the direction of the folding signal) than those obtained in the randomized variants (FIG. 3). Moreover, as was stated above, the maximal SCI value achieved in random is 0.2-0.42 while in wild-type 35%-100% of FE-selected positions possessed higher conservation levels (depending on serotype and the direction of the folding signal).

Conserved selection for strong/weak folding related signals cannot be explained basing only on dinucleotide composition. Arguably, the dinucleotide content is important when assessing the predicted free energy of RNA secondary structures [14-16]. In particular, it was suggested that disruption of naturally occurring biases in dinucleotide frequencies in genomic sequences of different organisms have been common sources of erroneous conclusions in previous studies [16,17]. To make sure that the presence of excess local secondary structure in coding regions of mRNA is not merely an artifact resulting from the failure to control for dinucleotide composition we verified the robustness of our findings by analyzing a dinucleotide-constrained randomization model controlling for the distribution of dinucleotide frequencies (see Materials and Methods section).

We found that as many as 60%, 52%, 49%, 34% of positions with significantly conserved signals related to strong folding and 62%, 58%, 43%, 44% of positions possessing weak folding signal conservation (identified with respect to evolutionary-constrained model for serotypes 1-4 correspondingly) overlapped with FE conserved signals identified with respect to dinucleotide-preserving randomization model (FIG. 3), and this overlap was not likely to appear in random (p-value<0.001 basing on conservation levels in 1000 randomized alignments; no overlap was observed in the case of the randomized genomes).

This result is further supporting the conjecture that dinucleotides alone cannot explain the majority of obtained FE signals identified with respect to the evolutionary-constrained model, and thus at least some of them undergo a conserved evolutionary selection for strong/weak folding and are not just artifacts of disrupting natural occurring biases in pairs of adjacent nucleotides.

The regions with significantly conserved strong/weak folding signals cannot be explained based only on sequence conservation. Although the nature of the evolutionary-constrained model excludes the possibility of significant FE signal conservation in regions with a low sequence variability across different viral variants (in such case the randomization will not have enough degrees of freedom to produce a sufficient variety of variants for a reliable statistical analysis) we decided to additionally explore the plausibility that conservation of folding signals may be a 'side effect' of conserved nucleotides composition or preference for specific synonymous codons (due to reasons not directly related to folding).

To this aim we quantified the variability among different sequences along the coding region, once with respect to a preference for synonymous codons and once with respect to nucleotides content, by considering an entropy based measure in each position in the coding region (see Material and Methods); this measure returns a value which ranges between 0 (no variability; i.e. a preference for a certain nucleotide/synonymous codon) and 1 (maximal variability; i.e. a uniform usage of all nucleotides/synonymous codons).

To assess the relationship between the conservation levels of FE related signals and sequence variability therein, we calculated Spearman correlations between: 1) the signal conservation profiles and 2) the nucleotide/synonymous variability profiles constructed by locally averaging the corresponding variability values in all 44 nt genomic intervals (the size of the intervals was chosen to match the 39 nt local windows in which the FE was predicted+the allowed 5 nt position shift in signal conservation analysis; see the Methods section and FIG. 1C); we also calculated, in a similar manner, the correlations between 1) the signal conservation profiles and 2) the variability profiles which were normalized with respect to their randomized variants (based on 1000 randomized alignments) to obtain z-score values (see Materials and Methods).

We found that the correlation between the FE signal conservation, and nucleotide and synonymous variability/z-score normalized variability is too low to conclude that regions with lower variability tend to have higher tendency for FE signal conservation. Specifically the correlation values were found to be confined in a narrow [−0.1 0.1] interval around zero for different types of variability profiles (FIG. 4B); i.e. less than 10% of the variance in signal conservation variable can be explained by the variability values.

These results support the conjecture that the conservation of FE related signals is not necessarily and only due to a preference of specific synonymous codons or conserved nucleotide content, and cannot be solely explained by the low sequence variability, thus supporting the evidence for a direct, conserved selection on positions for strong/weak folding.

Example 2

Comparison of Folding and Codon-Pair Deoptimized Sequences

For a particular wild-type sequence, we compared its folding deoptimized variant and a variant created according to the previously disclosed codon-pair deoptimization method [1]. The comparison was performed as follows:
a. A particular wild-type DENV-2 coding sequence was chosen
b. Intervals with significantly preserved selection (Preserved intervals) for strong folding and intervals with significantly preserved selection for weak folding were identified as described in the specification. Specifically, the selection preservation index was computed in 5 nt length SPI-intervals over all sequences in DENV serotype 2.
c. Clusters of Preserved intervals for strong and weak folding were computed as in 6; specifically the threshold D on distance between 5' ends of two consecutive intervals was set to 44 (39 nt—length windows in local folding energy was predicted+5 nt—offset used in selection preservation analysis), resulting in 65 clusters of strong folding Preserved Intervals and 73 clusters for weak folding Preserved Intervals.
d. For each cluster, one representative 39 nt window was chosen; resulting in 65 windows for strong folding, and 73 windows for weak folding (henceforth, we refer these intervals as selected windows).
e. The selected windows were deoptimized with respect to their folding strength; windows selected with respect to strong folding were manipulated to have a weaker folding, and vice versa—windows selected with respect to weak folding were manipulated to have a stronger folding. The deoptimization was performed via the Simulated Annealing optimization heuristics constrained to preserve the amino acid content and order of the wild-type windows.
f. For each selected window we computed the difference between the wild-type folding energy and the energy after folding deoptimization:

$$\Delta G_{FE\text{-}deopt} = FE_{wt} - FE_{FE\text{-}deopt}$$

g. A Codon-pair deoptimized variant of the wildtype sequence (a) was computed according to the previously disclosed procedure [1]. Specifically the Codon-Pair Score 0.026 of the wild-type sequence was deoptimized to −0.467 (the more negative the score is—the more underrepresented codon pairs with respect to human genome are used). h. Folding energy profiles of the wild-type (a) and codon-pair deoptimized (g) sequences were computed in 39 nt sliding windows (see 4):

$$F_{wildtype} = [F_{wt,1}, \ldots, F_{wt,i}, F_{wt,i+m}, \ldots, F_{wt,k}]$$

$$F_{CP\text{-}deopt} = [F_{CP\text{-}deopt,1}, \ldots, F_{CP\text{-}deopt,i}, F_{CP\text{-}deopt,i+m}, \ldots, F_{CP\text{-}deopt,k}]$$

i. Differences between folding energy profiles (h) of the wild-type (a) and codon-pair deoptimized (g) sequences were computed in a position-wise manner:

$$\Delta G_{CP\text{-}deopt} = [(F_{wt,1} - F_{CP\text{-}deopt,1}), \ldots, (F_{wt,k} - F_{CP\text{-}deopt,k})]$$

j. The distributions of changes in folding energies between the wild-type and folding-deoptimized ($\Delta G_{FE\text{-}deopt}$ in selected windows), and between wild-type and codon-pair deoptimized ($\Delta G_{CP\text{-}deopt}$ in all windows) were analyzed. As can be seen in FIGS. 8A-B, the $\Delta G_{FE\text{-}deopt}$ and $\Delta G_{CP\text{-}deopt}$ have different distributions with different mean values. Specifically:

For weak to strong deoptimization: only ~1% of windows for which folding in codon pair deoptimized sequence is weaker than in wildtype have $\Delta G_{CP\text{-}deopt} < -8$. In contrast, ~95% of 73 folding-deoptimized windows have $\Delta G_{FE\text{-}deopt} < -8$.

For strong to weak deoptimization: only ~11% of windows for which folding in codon pair deoptimized sequence is stronger than in wildtype have $\Delta G_{CP\text{-}deopt} > 5$. In contrast, ~57% of 65 selected windows have $\Delta G_{FE\text{-}deopt} > 5$.

Example 3

Algorithms

| Algorithm 1 (Farthest Sequence Sampling): |
|---|
| Input:     - a set of sequences S equipped with the diversity metric $d_S$;<br>              - an initial sequence $S_0 \in S$;<br>              - the desired number of selected sequences N;<br>Output:  - sampled sequences $S' = \{s_1, \ldots, s_N\}$;<br>1. $S' = \{s1\}$;<br>2. while $|S'| < N$<br>    2.1 Find the farthest sequence from $S'$:<br>    $s' = \arg\max_{s \in S} \{d_s = (s, S)\} = \arg\max_{s \in S'} \{d_s(s, s_i)\}$<br>    2.2 Update the set of selected sequences: $S' \leftarrow S' \cup \{s'\}$;<br>3. end |

| Algorithm 2 (HCUB randomization model): |
|---|
| Input:     - a wild type sequence $s = [s_1, \ldots, s_n]$;<br>Output:  - a randomized sequence $r = [r_1, \ldots, r_n]$;<br>1. For each amino acid A, compute its synonymous codons density function $F_A$<br>$$F_A(C_{A,i}) = q_{A,i}, \quad \sum_{i=1}^{m} q_{A,i} = 1$$<br>where $C_{A,i}$, $i = 1..m$, the m-th - synonymous codons of the amino acid A<br>2. For each i-th codon in s (coding amino acid Ai):<br>    2.1. $x \sim U(0,1)$<br>    2.2. If $x < q_{Ai,1}$ return $Ci = C_{Ai,1}$<br>         else if $x < q_{Ai,1} + q_{Ai,2}$ return $Ci = C_{Ai,2}$<br>         ...<br>         else if $x < q_{Ai,1} + \ldots + q_{Ai,m-1}$ return $Ci = C_{Ai,m-1}$<br>         else return $Ci = C_{Ai,m}$<br>    2.3. $r \leftarrow r + Ci$<br>3. return $r = [C1, \ldots, Ci, \ldots, Ck]$ |

| Algorithm 3 (VCUB randomization mode): |
|---|
| Input:     - a matrix of aligned wild type sequence<br>$$S = \begin{bmatrix} c_{11} & \cdots & c_{1k} \\ \vdots & \ddots & \vdots \\ c_{N1} & \cdots & c_{Nk} \end{bmatrix},$$<br>where $c_{ij}$ is the codon in position j in sequence i, N is the number of sequences and K is the number of codons in aligned sequences (each row is comprised of codons of a single sequence)<br>Output:  - a matrix of VCUB randomized sequences:<br>$$R = \begin{bmatrix} r_{11} & \cdots & r_{1k} \\ \vdots & \ddots & \vdots \\ r_{N1} & \cdots & r_{Nk} \end{bmatrix}$$<br>where $r_{ij}$ is the codon in position j in sequence i<br>1. For i-th column in S containing the i-th codon of each sequence $(1 \leq i \leq K)$<br>    1.1 For each amino acid, $A_{ij}$, that corresponds to the i-th column and appears in a subset $S_j$ of sequences ($S_j$ – integer indexes of the corresponding sequences):<br>        1.1.1. generate a random permutation of integers in $S_j$, $\sigma s_j$;<br>        1.1.2. For k = 1 to $|S_j|$<br>        $r_{i, S_j(k)} = \sigma_{s_j}(k)$<br>    1.2. $R \leftarrow [R + r_i]$, where $r_i$ is column i of randomized codons<br>2. Return the matrix R of VCUB randomized sequences. |

| Algorithm 4 (Local Genomic Feature Significance Test): |
|---|
| Input:     - a LGF profile of the wild type sequence S (the test statistics),<br>              $F = [f_1, \ldots, f_k]$,<br>              - a collection of N LGF profiles calculated on N randomizations of S (the null model),<br>$$\tilde{F} = [\tilde{F}_1 \cdots \tilde{F}_k] = \begin{bmatrix} \tilde{f}_{11} & \cdots & \tilde{f}_{1k} \\ \vdots & \ddots & \vdots \\ \tilde{f}_{n1} & \cdots & \tilde{f}_{nk} \end{bmatrix}$$<br>Output:  - p-value at position i, $p_i$<br>1. Compute the KST test on $\tilde{F}_i$: check the null hypothesis whether the sample of N i.i.d random variables $\tilde{F}_i = [\tilde{f}_{i1}, \ldots, \tilde{f}_{in}]^T$ is drawn from a Normal distribution $N(\hat{\mu}_i, \hat{\sigma}_i)$, where $\hat{\mu}_i$ and $\hat{\sigma}_i$ are the sample mean and standard deviation unbiased estimators correspondingly.<br>2. If KST accepted:<br>    2.1. $\tilde{F}_i$ is approximated by an underlying Normal distribution, and the one sided p-value is calculated analytically by:<br>        $P_i \leftarrow P_i^a = P(\tilde{F}_i < f_i) \sim N(f_i, \hat{\mu}_i, \hat{\sigma}_i)$<br>else<br>    2.2 calculate empiric p-value approximation:<br>$$p_i \leftarrow p_i^e = P(\tilde{F}_i < f) = \frac{1}{n}\sum_{k=1}^{n} I\{\tilde{f}_{ki} < x\}$$<br>3. Return $p_i$<br>The p-value approximations in this algorithm all correspond to a left-tailed test. Conversion to the right-tailed test and the two-tailed test is in all cases is *mutatis mutandis*. |

Algorithm 5 (Selection Concentration Profile):

Input: Selection Matrix $$S = \begin{bmatrix} \delta_{11} & \cdots & \delta_{1k} \\ \vdots & \ddots & \vdots \\ \delta_{n1} & \cdots & \delta_{nk} \end{bmatrix},$$

$$\delta_{ij} = \begin{cases} 1, & \text{position } j \text{ is salient in profile } i \\ 0, & \text{otherwise} \end{cases}$$

Output: - Selection Preservation Profile
$SCI = [SCI_1, \ldots, SCI_{k-w+1}]$

1. For each position i:
   1.1. Compute selection conservation submatrix corresponding to the window starting at position i:

$$S_i = \begin{bmatrix} \delta_{1,i} & \cdots & \delta_{1,max(i+w-1,k)} \\ \vdots & \vdots & \vdots \\ \delta_{n,i} & \cdots & \delta_{n,nmx(i+w-1,k)} \end{bmatrix}$$

1.2. Calculate the Selection Concentration Index:

$$SCI_i = \frac{1}{n} \sum_{k=1}^{n} \sum_{j=i}^{max(i+w-1,k)} \delta_{k,j}$$

1.3. $SCI[i] \leftarrow SCI_i$
2. Return SCI

---

Algorithm 6 (Selection Preservation Profile):

Input: -Selection Matrix $$S = \begin{bmatrix} \delta_{11} & \cdots & \delta_{1k} \\ \vdots & \ddots & \vdots \\ \delta_{n1} & \cdots & \delta_{nk} \end{bmatrix},$$

$$\delta_{ij} = \begin{cases} 1, & \text{position } j \text{ is salient in profile } i \\ 0, & \text{otherwise} \end{cases}$$

Output: - Selection Preservation Profile
$SPI = [SPI_1, \ldots, SPI_{k-w+1}]$

1. For each position i:
   1.1. Compute selection conservation submatrix corresponding to the window starting at position i:

$$S_i = \begin{bmatrix} \delta_{1,i} & \cdots & \delta_{1,max(i+w-1,k)} \\ \vdots & \vdots & \vdots \\ \delta_{n,i} & \cdots & \delta_{n,nmx(i+w-1,k)} \end{bmatrix}$$

1.2. Calculate the Selection Preservation Index:

$$SPI_i = \frac{r}{n}$$

1.3. $SPI[i] \leftarrow SPI_i$
2. Return SCI

---

One-Versus-Rest (OVR) Random Tests

Let P be some LGF profile and $\tilde{P} = \{\tilde{P}^k\}_{k=1}^n$, a set of its n randomized variants. Let T=G(S) be a vector (scalar) of some local (global) statistics on a set $S=S(P,\tilde{P})$ of single-sequence evolutionary salient local regions. The following algorithm tests the statistical significance of T:

Algorithm 7 (OVR)

Input:
   - a profile P ;
   - a set of its random variants $\tilde{P} = \{\tilde{P}^k\}_{k=1}^n$;
Output:
   - OVR p-value;
1. Initialize: $\tilde{T}[k] = 0, \forall k \in [1,\ldots,n]$
2. For k from 1 to n
   2.1. Identify salient regions in random variant k:
      $\tilde{S}^k \leftarrow S(\tilde{P}^k, \tilde{P}\backslash \tilde{P}^k)$
   2.2. Calculate statistics vector (scalar) T on salient regions:
      $\tilde{T}[k] +1 f \ G(\tilde{S}^k)$
end 3. Estimate $p - \text{value: } p_{OVR} \leftarrow \frac{1}{n} \sum_{k=1}^{n} I\{\tilde{T}[k] > T\}$ (if T is a vector, the statistical significance is estimates for each coordinate separately):

In some embodiments T is a Selection Concentration or Selection Preservation profile and G is a function for calculating SCI or SPI correspondingly.

---

Algorithm 8 (Significance Rank Aggregation)

Input: - a collection of M LGF profiles, $P = \{P_1, \ldots, P_M\}$
        - a collection of salient regions for each profile
Output: - top k salient regions
1. Initialize a L - length Votes vector:
   Aggregated rank $\leftarrow$ [0 0 0, . . . , 0], where L is profile length;
2. For each profile $P_i$
   2.1. Votes $\leftarrow$ [0 0 0, . . . , 0], where L is profile length;
   2.2. The number of votes given to a position is determined by its rank in a sorted profile and by the profile length L. A position will receive L votes if it is ranked first, L-1 points if it is ranked second, L-3 for being ranked in the third place, and so on:
      Ri $\leftarrow$ [sort positions in the profile corresponding to salient regions according to their significance levels in a descending order + append the remaining positions] = L-length vector of ranked positions
   2.3. Votes(Ri) $\leftarrow$ [L L-1 L-2 . . . 1]
   (positions which do not correspond to salient regions get vote = 0)
   2.4. Aggregated rank $\leftarrow$ Aggregated rank + Votes(Ri)
3. Return the top_k_salient_regions $\leftarrow$ k positions with top ranks in the Aggregated rank vector.

Algorithm 9 (construction of live attenuated genomes that maximize/minimize folding energy in selected regions while maintaining the encoded protein and the codon usage bias)

Input:
- a wild type genome sequence $s^{wt}$
- a collection of top K salient regions in $s^{wt}$ (respect to strong and weak folding)

Output:
- a library V of K candidate genomes of live attenuated vaccine

1. Initialize the library of live attenuated genomes:
$V \leftarrow \{\emptyset\}$
2. For $i^{th}$ salient region, $s_i^{wt}$ ($1 \le i \le K$):
2.1. Initialize the $i^{th}$ live attenuated genome with the wild-type sequence:
$v_i \leftarrow s^{wt}$
2.2. If $s_i^{wt}$ is selected with respect to strong folding:

$$s_i^* = \underset{s \in \{A,C,G,T\}^{L_i}}{\operatorname{argmax}} FE(s)$$

Else if $s_i^{wt}$ is selected with respect to weak folding:

$$s_i^* = \underset{s \in \{A,C,G,T\}^{L_i}}{\operatorname{argmin}} FE(s)$$

Subjected to
$Protein(s_i^*) = Protein(s_i^{wt})$
And
$CUB(s_i^*) = CUB(s_i^{wt})$
Where,

| | |
|---|---|
| $L_i$ | - size of the region (in nucleotides) |
| $\{A, C, G, T\}^{Li}$ | -a space of nucleotide sequences of size $L_i$ |
| $s_i^{wt} \in \{A, C, G, T\}^{Li}$ | -wild-type nucleotide sequence corresponding to the $i^{th}$ salient region |
| $s_i^* \in \{A, C, G, T\}^{Li}$ | - nucleotide sequence that maximizes the folding energy of the $i^{th}$ salient region subjected to constraints. |
| FE(s), Protein(s), CUB(s) | - Folding energy, protein and codon usage bias encoded by a nucleotide sequence s. |

2.3. Replace the nucleotides in the $i^{th}$ salient region with the nucleotides that solve the optimization problem in 2.2.:
$v_i(s_i^{wt}) \leftarrow s_i^*$
Sequence outside the $i^{th}$ region is not modified.
2.4. Add the $i^{th}$ live attenuated genome to the library:
$V \leftarrow V \cup v_i$
3. return V Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Coleman J R, Papamichail D, Skiena S, Futcher B, Wimmer E, et al. (2008) Virus attenuation by genome-scale changes in codon pair bias. Science (New York, N.Y.) 320: 1784-1787. doi:10.1126/science.1155761.
2. Sievers F, Wilm A, Dineen D, Gibson T J, Karplus K, et al. (2011) Fast, scalable generation of high-quality protein multiple sequence alignments using Clustal Omega. Molecular systems biology 7: 539. doi:10.1038/msb.2011.75.
3. Altschul S, Erickson B (1985) Significance of nucleotide sequence alignments: a method for random sequence permutation that preserves dinucleotide and codon usage. Mol Biol Evol 2: 526-538.
4. Zhang Y, Ponty Y, Blanchette M, Lécuyer E, Waldispal J (2013) SPARCS: a web server to analyze (un)structured regions in coding RNA sequences. Nucleic acids research 41: W480-5. doi:10.1093/nar/gkt461.
5. Lorenz R, Bernhart S H, Höner Zu Siederdissen C, Tafer H, Flamm C, et al. (2011) ViennaRNA Package 2.0. Algorithms for molecular biology: AMB 6: 26. doi:10.1186/1748-7188-6-26.
6. Mathews D H (2006) Revolutions in RNA secondary structure prediction. Journal of molecular biology 359: 526-532. doi:10.1016/j.jmb.2006.01.067.
7. Mathews D H, Sabina J, Zuker M, Turner D H (1999) Expanded sequence dependence of thermodynamic parameters improves prediction of RNA secondary structure. Journal of molecular biology 288: 911-940. doi:10.1006/jmbi.1999.2700.
8. Wuchty S, Fontana W, Hofacker I L, Schuster P (1999) Complete suboptimal folding of RNA and the stability of secondary structures. Biopolymers 49: 145-165. doi:10.1002/(SICI)1097-0282(199902)49:2<145::AID-BIP4>3.0.CO;2-G.
9. Zanini F, Neher R A (2013) Quantifying selection against synonymous mutations in HIV-1 env evolution. Journal of virology 87: 11843-11850. doi:10.1128/JVI.01529-13.
10. Jackson R J (2005) Alternative mechanisms of initiating translation of mammalian mRNAs. Biochemical Society transactions 33: 1231-1241. doi:10.1042/BST20051231.
11. Selby C P, Drapkin R, Reinberg D, Sancar A (1997) RNA polymerase II stalled at a thymine dimer: footprint and effect on excision repair. Nucleic acids research 25: 787-793.
12. Tuller T, Zur H (2014) Multiple roles of the coding sequence 5' end in gene expression regulation. Nucleic Acids Research 43: 13-28. doi:10.1093/nar/gku1313.
13. Alcaraz-Estrada S L, Yocupicio-Monroy M, del Angel R M (2010) Insights into dengue virus genome replication. Future Virology 5: 575-592. doi:10.2217/fv1.10.49.
14. Zuker M, Stiegler P (1981) Optimal computer folding of large RNA sequences using thermodynamics and auxiliary information. Nucleic acids research 9: 133-148.
15. Nussinov R (1984) Strong doublet preferences in nucleotide sequences and DNA geometry. Journal of molecular evolution 20: 111-119.
16. Workman C, Krogh A (1999) No evidence that mRNAs have lower folding free energies than random sequences with the same dinucleotide distribution. Nucleic acids research 27: 4816-4822.
17. Rivas E, Eddy S R (2000) Secondary structure alone is generally not statistically significant for the detection of noncoding RNAs. Bioinformatics (Oxford, England) 16: 583-605.

SEQUENCE LISTING

The patent contains a lengthy sequence listing. A copy of the sequence listing is available in electronic form from the USPTO web site (https://seqdata.uspto.gov/?pageRequest=docDetail&DocID=US11795440B2). An electronic copy of the sequence listing will also be available from the USPTO upon request and payment of the fee set forth in 37 CFR 1.19(b)(3).

What is claimed is:

1. A method of making an attenuated form of a virulent virus genome, the method comprising:
   a. receiving a sequence of an RNA of said virulent virus encoding a viral protein or a nucleic acid sequence transcribable to said RNA; and
   b. synonymously substituting at least one nucleotide in a region of evolutionarily conserved local RNA folding energy of said RNA to another nucleotide,
   wherein said region of evolutionarily conserved local RNA folding energy comprises folding energy below a predetermined threshold and said substitution increases said folding energy, or said region of evolutionarily conserved RNA folding energy comprises folding energy above a predetermined threshold and said substitution decreases said folding energy, wherein said predetermined threshold is derived from the average local folding energy of a randomized sequence of the virulent virus, wherein said randomized sequence encodes an amino acid sequence which is identical to the corresponding non-randomized amino acids sequence of said virulent virus;
   and wherein said viral protein encoded by the synonymously substituted RNA comprises an amino acid sequence which is identical to the amino acid sequence of said viral protein of the virulent virus and said at least one substitution decreases replicative fitness of said attenuated form of a virus as compared to said virulent virus;
   thereby making an attenuated form of a virulent virus genome.

2. The method of claim 1, further comprising inserting said synonymously substituted sequence of said RNA in place of said received RNA sequence in the genome of said virulent virus.

3. The method of claim 1, further comprising mutating the RNA genome of said virulent virus to produce said synonymously substituted RNA.

4. The method of claim 1, further comprising mutating the DNA genome of said virulent virus to produce DNA encoding said synonymously substituted RNA.

5. The method of claim 1, wherein the untranslated region of said RNA is identical to the untranslated region of the corresponding RNA of the virulent virus.

6. The method of claim 1, wherein the virulent virus:
   a. is selected from a natural isolate and a mutant of a natural isolate;
   b. infects an animal or a plant, optionally wherein the animal is a human; or
   c. induces a protective immune response in an animal host.

7. The method of claim 1, comprising synonymously substituting a plurality of nucleotides, wherein a synonymous substitution is present at each region of evolutionarily conserved local RNA folding energy for which a synonymous substitution exists that increases folding energy of a region comprising folding energy below said predetermined threshold or decreases folding energy of a region comprising folding energy above said predetermined threshold.

8. The method of claim 1, wherein said region of evolutionarily conserved local RNA folding energy is increased or decreased by a maximum possible amount while maintaining said amino acid sequence.

9. The method of claim 1, comprising synonymously substituting a nucleotide in at least 10% of the regions of evolutionarily conserved local RNA folding energy throughout the genome of said virulent virus.

10. The method of claim 1, wherein said RNA encodes more than one protein.

11. The method of claim 1, wherein said RNA encodes a capsid protein.

12. The method of claim 1, wherein said virulent virus is selected from the group consisting of dengue virus, poliovirus, rhinovirus, influenza virus, severe acute respiratory syndrome (SARS) coronavirus, Human Immunodeficiency Virus (HIV), Hepatitis C Virus (HCV), infectious bronchitis virus, Ebolavirus, Marburg virus, West Nile disease virus, Epstein-Barr virus (EBV), yellow fever virus, Zika virus, and flavivirus.

13. The method of claim 1, wherein said at least one nucleotide substituted to another nucleotide maintains the overall codon usage bias, GC content or both of said virulent virus.

14. The method of claim 1, comprising producing a total change in local folding energy of at least 20% of the maximum change in local folding energy that can be generated by modifying all regions of evolutionarily conserved local RNA folding energy for which a synonymous substitution exists that increases folding energy of a region comprising folding energy below said predetermined threshold or decreases folding energy of a region comprising folding energy above said predetermined threshold.

15. The method of claim 1, wherein said substitution increase said folding energy by greater than 3 kcal/mol or decreases said folding energy by greater than 9 kcal/mol.

16. The method of claim 1, wherein said randomized sequence further retains the dinucleotide content, GC content, codon bias or a combination thereof of said virulent virus.

17. The method of claim 1, wherein said randomized sequence of the virulent virus is at least 100 randomized sequences of the virulent virus.

18. A method of making an attenuated form of a virulent virus, the method comprising producing an attenuated viral genome by the method of claim 1 and inserting said attenuated viral genome into a virus.

19. The method of claim 18, wherein said virus lacks an endogenous genome.

20. A method of making an attenuated form of a virulent virus, the method comprising mutating the RNA genome of said virulent virus to synonymously substitute at least one nucleotide in a region of evolutionarily conserved local RNA folding energy to another nucleotide or mutating the DNA genome of said virulent virus to synonymously substitute at least one nucleotide in a region encoding a region of evolutionarily conserved local RNA folding energy to another nucleotide, wherein said region of evolutionarily conserved local RNA folding energy comprises folding energy below a predetermined threshold and said substitution increases said folding energy, or said region of evolutionarily conserved RNA folding energy comprises folding energy above a predetermined threshold and said substitution decreases said folding energy, wherein said predetermined threshold is derived from the average local folding energy of a randomized sequence of the virulent virus, wherein said randomized sequence encodes an amino acid sequence which is identical to the corresponding non-randomized amino acids sequence of said virulent virus;

and wherein a viral protein encoded by the mutated genome comprises an amino acid sequence which is identical to the amino acid sequence of said viral protein encoded by the genome of the virulent virus and said at least one substitution decreases replicative fitness of said attenuated form of a virus as compared to said virulent virus;

thereby making an attenuated form of a virulent virus.

* * * * *